(12) United States Patent
Schwientek et al.

(10) Patent No.: US 7,078,206 B2
(45) Date of Patent: *Jul. 18, 2006

(54) UDP-N-ACETYLGLUCOSAMINE: GALACTOSE-β1,3-N-ACETYLGALACTOSAMINE-α-R/ (GLCNAC TO GALNAC) β1,6N-ACETYLGLUCOSAMINYLTRANSFERASE, C2GNT3

(75) Inventors: Tilo Schwientek, Brønshøj (DK); Henrik Clausen, Holte (DK)

(73) Assignee: GlycoZym ApS, Holte (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,723

(22) Filed: May 11, 2004

(65) Prior Publication Data

US 2004/0203111 A1    Oct. 14, 2004

Related U.S. Application Data

(60) Continuation of application No. 10/084,406, filed on Feb. 25, 2002, now Pat. No. 6,794,169, which is a division of application No. 09/645,192, filed on Aug. 24, 2000, now Pat. No. 6,635,461.

(60) Provisional application No. 60/150,488, filed on Aug. 24, 1999.

(51) Int. Cl.
*C12N 9/10* (2006.01)
*C07K 1/00* (2006.01)

(52) U.S. Cl. .......................... 435/193; 530/350
(58) Field of Classification Search ............... 435/193, 435/320.1, 325, 252.3, 6; 530/350
See application file for complete search history.

(56) References Cited

U.S. PATENT DOCUMENTS

2002/0045202 A1 * 4/2002 Korczak et al. ............... 435/15

OTHER PUBLICATIONS

Schwientek et al., GenEmbl Database, accession No. AF132035, Apr. 2000.*

* cited by examiner

*Primary Examiner*—Maryam Monshipouri
(74) *Attorney, Agent, or Firm*—Darby & Darby

(57) ABSTRACT

A novel gene defining a novel human UDP-GlcNAc: Galβ1-3GalNAcα β1,6GlcNAc-transferase, termed C2GnT3, with unique enzymatic properties is disclosed. The enzymatic activity of C2GnT3 is shown to be distinct from that of previously identified enzymes of this gene family. The invention discloses isolated DNA molecules and DNA constructs encoding C2GnT3 and derivatives thereof by way of amino acid deletion, substitution or insertion exhibiting C2GnT3 activity, as well as cloning and expression vectors including such DNA, cells transfected with the vectors, and recombinant methods for providing C2GnT3. The enzyme C2GnT3 and C2GnT3-active derivatives thereof are disclosed, in particular soluble derivatives comprising the catalytically active domain of C2GnT3. Further, the invention discloses methods of obtaining 1,6-N-acetylglucosaminyl glycosylated saccharides, glycopeptides or glycoproteins by use of an enzymatically active C2GnT3 protein or fusion protein thereof or by using cells stably transfected with a vector including DNA encoding an enzymatically active C2GnT3 protein as an expression system for recombinant production of such glycopeptides or glycoproteins. Methods are disclosed for the identification of agents with the ability to inhibit or stimulate the biological activity of C2GnT3. Furthermore, methods of using C2GnT3 in the structure-based design of inhibitors or stimulators thereof are also disclosed in the invention. Also a method for the identification of DNA sequence variations in the C2GnT3 gene by isolating DNA from a patient, amplifying C2GnT3-coding exons by PCR, and detecting the presence of DNA sequence variation, are disclosed.

4 Claims, 5 Drawing Sheets

Fig.1

C2GnT3

```
  1   M  K  I  F  K  C  Y  F  K  H  T  L  Q  Q  K  V  F  I  L  F  L  T  L  H  L  L  S  L  L  K  L  L  N  V  R  R  L  F  P  Q      40
  1   ATGAAGATATTCAAATGTTATTTTAAACATACCCTACAGCAGAAAGTTTTCATCCTGTTTTTAACCCTGCATCTTCTTTCTCTTCTTAAGCTTCTAAATGTGAGACGACTCTTTCCGCAA   120

41   K  D  I  Y  L  V  E  Y  S  L  S  T  S  P  F  V  R  N  R  Y  T  H  V  K  D  E  V  R  Y  E  V  N  C  S  G  I  Y  E  Q  E      80
121   AAAGACATTTACTTGGTTGAGTACTCCCTAAGTACCTCGCCTTTGTAAGAAACAGATACACTGTTAAGGATGAAGTCAGGTATGAAGTTAACTGTTCGGGTATCTATGAACAGGAG       240

81   P  L  E  I  G  K  S  L  E  I  R  R  R  D  I  I  D  L  E  D  D  D  V  A  M  T  S  D  C  D  I  Y  Q  T  L  R  G  Y  A       120
241   CCTTTGGAAATTGGAAAGAGTCTGGAAATAAGAAGAAGAGACATCATTGACTTGGAGGATGATGATGTTGCGGCAATGACCAGTGACTGTGACATTTATCAGACTCTAAGAGGTTATGCT   360

121   Q  K  L  V  S  K  E  E  K  S  F  P  I  A  Y  S  L  V  V  H  K  D  A  I  M  V  E  R  L  I  H  A  I  Y  N  Q  H  N  I  Y      160
361   CAAAAGCTTGTCTCAAAGGAGGAGAAAAGCTTCCCAATAGCCTATTCTTTGGTTGTCCACAAAGATGCAATTATGGTTGAAAGGCTTATCCATGCTATATACAACCAGCACAATATTTAC   480

161   C  I  H  Y  D  R  K  A  P  D  T  F  K  V  A  M  N  N  L  A  K  C  F  S  N  I  F  I  A  S  K  L  E  A  V  E  Y  A  H  I      200
481   TGCATCCATTATGATCGTAAGGCACCTGATACCTTCAAAGTTGCCATGAACAATTTAGCCAAGTGCTTCTCCAATATTTTCATTGCTTCCAAATTAGAGGCTGTGGAATATGCCCACATT   600

201   S  R  L  Q  A  D  L  N  C  L  S  D  L  L  K  S  S  I  Q  W  K  Y  V  I  N  L  C  G  Q  D  F  P  L  K  S  N  F  E  L  V      240
601   TCCAGACTCCAGGCTGATTTAAATTGCTTGTCGGACCTTCTGAAGTCTTCAATCCAGTGGAAATATGTTATCAACTTGTGTGGGCAAGATTTTCCCCTGAAGTCAAATTTTGAATTGGTG   720

241   S  E  L  K  K  L  N  G  A  N  M  L  E  T  V  K  P  P  N  S  K  L  E  R  F  T  Y  H  H  E  L  R  R  V  P  Y  E  Y  V  K      280
721   TCAGAGTTGAAAAAACTCAATGGAGCAAATATGTTGGAGACGGTCAAACCCCCAAACAGTAAATTGGAAAGATTCACTTACCATCATGAACTTAGAAGGGTGCCTTATGAATATGTGAAG   840

281   L  P  I  R  T  N  I  S  K  E  A  P  P  H  N  I  Q  I  F  V  G  S  A  Y  F  V  L  S  Q  A  F  V  K  Y  I  F  N  N  S  I      320
841   CTACCAATAAGGACAAACATCTCCAAGGAGGCACCCCCCCATAACATTCAGATATTTGTTGGCAGTGCCTATTTTGTTTTAAGTCAAGCATTTGTTAAATATATTTTCAACAACTCCATC   960

321   V  Q  D  F  F  A  W  S  K  D  T  Y  S  P  D  E  H  F  W  A  T  L  L  I  R  V  P  G  E  I  S  R  S  A  Q  D  V  S       360
961   GTTCAAGACTTTTTTGCCTGGTCCTAAAGACACTACTCCCTGATGAGCACTTTTGGGCTACCTTGCTGATTCGGGTTCCAGGAGAATACCTGGGAGATTTCAGATACGCCAGGATGTGTCT  1080

361   D  L  Q  S  K  T  R  L  V  K  W  N  Y  Y  E  G  E  F  F  Y  P  S  C  T  G  S  H  L  R  S  V  C  I  Y  G  A  E  L  R  W      400
1081  GATCTGCAGAGTAAGACTCGCCTTGTCAAGTGGAATTACTATGAAGGCTTTTTCTATCCCAGTTGTACTGGATCTCACCTTCGAAGCGTGTGTATTTATGGAGCGCAGAATTAAGGTGG   1200

401   L  I  K  D  G  H  W  F  A  N  K  F  D  S  K  V  D  P  L  I  K  C  L  A  E  K  L  E  E  Q  Q  R  D  W  I  T  L  P  S       440
1201  CTTATCAAAGATGGACATTGGTTTGCTAATAAATTTGATTCTAAGGTGGACCCTCTTATCAAATGCTTGGCAGAAAAGCTTGAAGAACAGCAGAGAGACTGGATCACTTTGCCCTCA    1320

441   E  K  L  F  M  D  R  N  L  T  T  T  S  *                                                                                    453
1321  GAAAAGTTATTTATGGATAGAAATCTCACTACCACATCATGA                                                                                  1362
```

Fig. 2

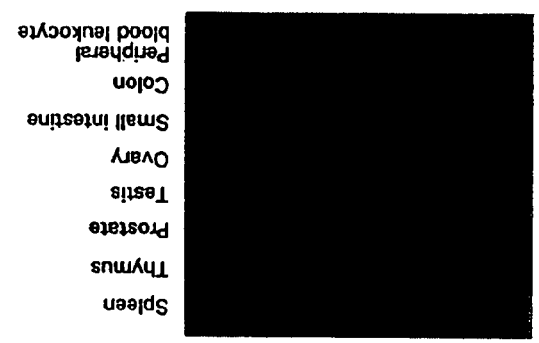
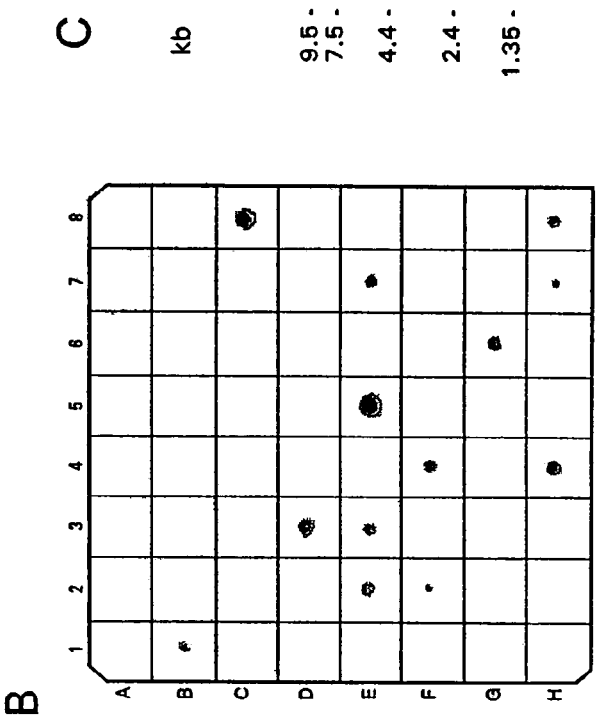
Fig. 3

US 7,078,206 B2

UDP-N-ACETYLGLUCOSAMINE: GALACTOSE-β1,3-N-ACETYLGALACTOSAMINE-α-R/ (GLCNAC TO GALNAC) β1,6N-ACETYLGLUCOSAMINYLTRANSFERASE, C2GNT3

This application is a continuation of U.S. Ser. No. 10/084,406, filed Feb. 25, 2002 now U.S. Pat. No. 6,794,169 issued Sep. 21, 2004, which is a divisional of U.S. Ser. No. 09/645,192, filed Aug. 24, 2000, now U.S. Pat. No. 6,635,461, issued Oct. 21, 2003, which claims priority to U.S. Ser. No. 60/150,488, filed Aug. 24, 1999. Each of these prior applications is incorporated by reference in its entirety.

TECHNICAL FIELD

The present invention relates generally to the biosynthesis of glycans found as free oligosaccharides or covalently bound to proteins and glycolipids. In particular, this invention relates to a family of nucleic acids encoding UDP-N-acetylglucosamine: N-acetylgalactosamine-β1,6-N-acetylglucosaminyltransferases (Core-β1,6-N-acetylglucosaminyltransferases), which add N-acetylglucosamine to the hydroxy group at C6 of 2-acetamido-2-deoxy-D-galactosamine (GalNAc) in O-glycans of the core 1 and the core 3 type thereby forming the core 2 and core 4 types. Previously two members of this family have been identified and designated C2GnT1 and C2GnT2.

This invention is more particularly related to a gene encoding a third member of this family of O-glycan β1,6-N-acetylglucosaminyltransferases, termed C2GnT3, probes to the DNA encoding C2GnT3, DNA constructs comprising DNA encoding C2GnT3, recombinant plasmids and recombinant methods for producing C2GnT3, recombinant methods for stably transforming or transfecting cells for expression of C2GnT3, methods for identification of agents with the ability to inhibit or stimulate C2GnT3 biological activity, and methods for identification of DNA polymorphism in patients. In the U.S.Provisional Patent Application No. 60/150,488 filed on Aug. 24, 1999, from which the present application claims priority, this novel Core 2 β6GlcNAc-transferase isoform was identified and designated C2GnTII. The designation C2GnTII has here been replaced by the designation C2GnT3 in accordance with its scientific publication (14).

BACKGROUND OF THE INVENTION

O-linked protein glycosylation involves an initiation stage in which a family of N-acetylgalactosaminyltransferases catalyzes the addition of N-acetylgalactosamine to Serine or Threonine residues (1). Further assembly of O-glycan chains involves several sucessive or alternative biosynthetic reactions: i) formation of simple mucin-type core 1 structures by UDP-Gal: GalNAcα-R β1,3Gal-transferase activity; ii) conversion of core 1 to complex-type core 2 structures by UDP-GlcNAc: Galα1-3GalNAcα-R β1,6GlcNAc-transferase activities; iii) direct formation of complex mucin-type core 3 by UDP-GlcNAc: GalNAcα β1,3GlcNAc-transferase activities; and iv) conversion of core 3 to core 4 by UDP-GlcNAc: GlcNAcβ1-3GalNAcα-R β1,6GlcNAc-transferase activity. The formation of β1,6GlcNAc branches (reactions ii and iv) may be considered a key controlling event of O-linked protein glycosylation leading to structures produced upon differentiation and malignant transformation (2-6). For example, increased formation of GlcNAc□1-6GalNAc branching in O-glycans has been demonstrated during T-cell activation, during the development of leukemia, and for immunodeficiencies like Wiskott-Aldrich syndrome and AIDS (7; 8). Core 2 branching may play a role in tumor progression and metastasis (9). In contrast, many carcinomas show changes from complex O-glycans found in normal cell types to immaturely processed simple mucin-type O-glycans such as T (Thomsen-Friedenreich antigen; Galβ1-3GalNAcα1-R), Tn (GalNAcα1-R), and sialosyl-Tn (NeuAcα2-6GalNAcα1-R) (10). The molecular basis for this has been extensively studied in breast cancer, where it was shown that specific downregulation of a core 2 β6GlcNAc-transferase was responsible for the observed lack of complex type O-glycans on the mucin MUC1 (6). O-glycan core assembly may therefore be controlled by inverse changes in the expression level of Core-β1,6-N-acetylglucosaminyl-transferases and the sialyltransferases forming sialyl-T and sialyl-Tn.

Interestingly, the metastatic potential of tumors has been correlated with increased expression of core 2 β6GlcNAc-transferase activity (5). The increase in core 2 β6GlcNAc-transferase activity was associated with increased levels of poly N-acetyllactosamine chains carrying sialyl-Le$^x$, which may contribute to tumor metastasis by altering selectin-mediated adhesion (4; 11). The control of O-glycan core assembly is regulated by the expression of key enzyme activities; however, epigenetic factors including posttranslational modification, topology, or competition for substrates may also play a role in this process (11).

Changes in surface carbohydrates of T-cells have been identified during development and activation. O-glycan branches of the core 2 type are restricted to immature thymocytes of the thymal cortex but are no longer exposed on the surface of mature medullary thymocytes (17). Core 2 structures on T-cell surface proteins are ligands for the S-type lectin galectin-1, which participates in thymocyte-thymic epithelia interaction (18). The elimination of Core 2 structures from the thymocyte cell surface was found to be essential for controlled apoptosis mediated by galectin-1 (19).

Core 2 β6GlcNAc-transferase activity is carried out by more than one enzyme isoform. The first Core 2 β6GlcNAc-transferase isoform was initially identified as a critical enzyme in blood cell development and differentiation and designated leukocyte form or L-Form (C2GnT-L)(12). The gene encoding C2GnT-L has been cloned by expression cloning from a cDNA library of the human promyelocytic leukemia cell line HL-60 (13). This gene has now been renamed as C2GnT1 (14). Using the C2GnT1 sequence as a probe for BLAST analysis of the human expressed sequence tag database, a homologous gene encoding a second Core 2 β6GlcNAc-transferase isoform has been identified and designated C2/4GnT (15) and C2GnT-M (16). This gene has now been renamed as C2GnT2 (14).

C2GnT1 was predicted to control synthesis of core 2 selectin ligands in leukocytes and lymphoid tissues, however, mice deficient in C2GnT1 exhibited only partial reduction in selectin ligand production and no significant changes in lymphocyte homing properties (Ellies, L. G., et al. 1998, Immunity 9: 881–890). One possible explanation for these results would be the expression of additional Core 2 β6GlcNAc-transferases. C2GnT2 does not appear to be a candidate, as its expression pattern is restricted to mucous secreting organs (15, 16).

Consequently, there exists a need in the art for detecting as yet unidentified UDP-N-acetylglucosamine: Galactose-β1,3-N-acetylgalactosamine-α-R (GlcNAc to GalNAc) β1-6 N-acetylglucosaminyltransferases and identifying the primary structures of the genes encoding such enzymes. The present invention meets this need, and further presents other related advantages.

SUMMARY OF THE INVENTION

The present invention provides isolated nucleic acids encoding human UDP-N-acetylglucosamine: N-acetylgalactosamine β1,6 N-acetylglucosaminyltransferase 3 (C2GnT3), including cDNA and genomic DNA. C2GnT3 has acceptor substrate specificities comparable to C2GnT1 (14). The complete nucleotide sequence encoding C2GnT3 is set forth in SEQ ID NO: 1 and in FIG. 1.

Variations in one or more nucleotides may exist among individuals within a population due to natural allelic variation. Any and all such nucleic acid variations are within the scope of the invention. DNA sequence polymorphisms may also occur which lead to changes in the amino acid sequence of a C2GnT3 polypeptide. These amino acid polymorphisms are also within the scope of the present invention. In addition, species variations i.e. variations in nucleotide sequence naturally occurring among different species, are within the scope of the invention.

Among Core 2 β6GlcNAc-transferases, C2GnT3 appears to be the dominant isoform in thymus (14). Thus, C2GnT3 is likely to have important functions during thymocyte development as well as T-cell maturation and homing (14). The identification of agents with the ability to inhibit or stimulate C2GnT3 enzymatic activity therefore has the potential for both diagnostic and therapeutic purposes of related diseases.

Access to the gene encoding C2GnT3 allows production of a glycosyltransferase for use in formation of core 2-based O-glycan modifications on oligosaccharides, glycoproteins and glycosphingolipids. This enzyme can be used, for example, in pharmaceutical or other commercial applications that require synthetic addition of core 2-based O-glycans to these or other substrates, in order to produce appropriately glycosylated glycoconjugates having particular enzymatic, immunogenic, or other biological and/or physical properties.

In one aspect, the invention encompasses isolated nucleic acids comprising the nucleotide sequence of nucleotides 1–1362 as set forth in FIG. 1 or sequence-conservative or function-conservative variants thereof. Also provided are isolated nucleic acids hybridizable with nucleic acids having the sequence as set forth in FIG. 1 or fragments thereof or sequence-conservative or function-conservative variants thereof; preferably, the nucleic acids are hybridizable with C2GnT3 sequences under conditions of intermediate stringency, and, most preferably, under conditions of high stringency. In one embodiment, the DNA sequence encodes the amino acid sequence shown in FIG. 1, from methionine (amino acid no. 1) to serine (amino acid no. 453). In another embodiment, the DNA sequence encodes an amino acid sequence comprising a sequence from proline (no. 39) to serine (no. 453) of the amino acid sequence set forth in FIG. 1.

In a related aspect, the invention provides nucleic acid vectors comprising C2GnT3 DNA sequences, including but not limited to those vectors in which the C2GnT3 DNA sequence is operably linked to a transcriptional regulatory element, with or without a polyadenylation sequence. Cells comprising these vectors are also provided, including without limitation transiently and stably expressing cells. Viruses, including bacteriophages, comprising C2GnT3-derived DNA sequences are also provided. The invention also encompasses methods for producing C2GnT3 polypeptides. Cell-based methods include without limitation those comprising: introducing into a host cell an isolated DNA molecule encoding C2GnT3, or a DNA construct comprising a DNA sequence encoding C2GnT3; growing the host cell under conditions suitable for C2GnT3 expression; and isolating C2GnT3 produced by the host cell. A method for generating a host cell with de novo stable expression of C2GnT3 comprises: introducing into a host cell an isolated DNA molecule encoding C2GnT3 or an enzymatically active fragment thereof (such as, for example, a polypeptide comprising amino acids 39–453 of the sequence set forth FIG. 1), or a DNA construct comprising a DNA sequence encoding C2GnT3 or an enzymatically active fragment thereof; selecting and growing host cells in an appropriate medium; and identifying stably transfected cells expressing C2GnT3. The stably transfected cells may be used for the production of C2GnT3 enzyme for use as a catalyst and for recombinant production of peptides or proteins with appropriate glycosylation. For example, eukaryotic cells, whether normal or diseased cells, having their glycosylation pattern modified by stable transfection as above, or components of such cells, may be used to deliver specific glycoforms of glycopeptides and glycoproteins, such as, for example, as immunogens for vaccination.

In yet another aspect, the invention provides isolated C2GnT3 polypeptides, including without limitation polypeptides having the sequence set forth in FIG. 1, polypeptides having the sequence of amino acids 39–453 as set forth in FIG. 1, and a fusion polypeptide consisting of at least amino acids 39–453 as set forth in FIG. 1 fused in frame to a second sequence, which may be any sequence that is compatible with retention of C2GnT3 enzymatic activity in the fusion polypeptide.

Suitable second sequences include without limitation those comprising an affinity ligand or a reactive group.

In a related aspect, methods are disclosed for the identification of agents with the ability to inhibit or stimulate the enzymatic activity of C2GnT3. Assays utilizing C2GnT3 to screen for potential inhibitors or stimulators thereof are encompassed by the invention. Furthermore, methods of using C2GnT3 in the structure-based design of inhibitors or stimulators thereof are also an aspect of the invention. Such a design would comprise the steps of determining the three-dimensional structure of the C2GnT3 polypeptide, analyzing the three-dimensional structure for the likely binding sites of donor and/or acceptor substrates, synthesis of a molecule that incorporates a predictive reactive site, and determining the inhibiting or stimulating activity of the molecule.

In another aspect of the present invention, methods are disclosed for screening for mutations in the coding region of the C2GnT3 gene using genomic DNA isolated from, e.g., blood cells of patients. In one embodiment, the method comprises: isolation of DNA from a patient; PCR amplification of the coding exon; DNA sequencing of amplified exon DNA fragments and establishing therefrom potential structural defects of the C2GnT3 gene associated with disease.

In accordance with an aspect of the invention there is provided a method of, and products for (i.e. kits), diagnosing and monitoring conditions mediated by C2GnT3 by determining, in a biological sample, the presence of nucleic acid molecules and polypeptides of the invention.

Still further the invention provides a method for evaluating a test compound for its ability to modulate the biological activity of a C2GnT3 polypeptide of the invention. For example, a substance that inhibits or enhances the catalytic activity of a C2GnT3 polypeptide may be evaluated. "Modulate" refers to a change or an alteration in the biological activity of a polypeptide of the invention. Modulation may be an increase or a decrease in activity, a change in characteristics, or any other change in the biological, functional, or immunological properties of the polypeptide.

Compounds which modulate the biological activity of a polypeptide of the invention may also be identified using the methods of the invention by comparing the pattern and level of expression of a nucleic acid molecule or polypeptide of the invention in biological samples, tissues and cells, in the presence, and in the absence of the compounds.

In an embodiment of the invention a method is provided for screening a compound for effectiveness as an antagonist of a polypeptide of the invention, comprising the steps of a) contacting a sample containing said polypeptide with a compound, under conditions wherein antagonist activity of said polypeptide can be detected, and b) detecting antagonist activity in the sample.

Methods are also contemplated that identify compounds or substances (e.g. polypeptides), which interact with C2GnT3 nucleic acid regulatory sequences (e.g. promoter sequences, enhancer sequences, negative modulator sequences).

The nucleic acids, polypeptides, and substances and compounds identified using the methods of the invention, may be used to modulate the biological activity of a C2GnT3 polypeptide of the invention, and they may be used in the treatment of conditions mediated by C2GnT3 such as proliferative diseases including cancer, and thymus-related disorders. Accordingly, the nucleic acids, polypeptides, substances and compounds may be formulated into compositions for administration to individuals suffering from one or more of these conditions. Therefore, the present invention also relates to a composition comprising one or more of a polypeptide, nucleic acid molecule, or substance or compound identified using the methods of the invention, and a pharmaceutically acceptable carrier, excipient or diluent. A method for treating or preventing these conditions is also provided comprising administering to a patient in need thereof, a composition of the invention.

The present invention in another aspect provides means necessary for production of gene-based therapies directed at the thymus. These therapeutic agents may take the form of polynucleotides comprising all or a portion of a nucleic acid of the invention comprising a regulatory sequence of a C2GnT3 nucleic acid placed in appropriate vectors or delivered to target cells in more direct ways.

Having provided a novel C2GnT3, and nucleic acids encoding same, the invention accordingly further provides methods for preparing oligosaccharides. In specific embodiments, the invention relates to a method for preparing an oligosaccharide comprising contacting a reaction mixture comprising a donor substrate, and an acceptor substrate in the presence of a C2GnT3 polypeptide of the invention.

In accordance with a further aspect of the invention, there are provided processes for utilizing polypeptides or nucleic acid molecules, for in vitro purposes related to scientific research, synthesis of DNA, and manufacture of vectors.

These and other aspects of the present invention will become evident upon reference to the following detailed description and drawings.

BRIEF DESCRIPTION OF THE DRAWINGS

FIG. 1 depicts the DNA sequence of the C2GnT3 gene (accession #AF132035; SEQ ID NO: 1) and the predicted amino acid sequence of C2GnT3 (SEQ ID NO: 2). The amino acid sequence is shown in single letter code. The hydrophobic segment representing the putative transmembrane domain is double underlined. Four consensus motifs for N-glycosylation are indicated by asterisks. The location of the primers used for preparation of the expression constructs are indicated by single underlining.

FIG. 2 is an illustration of a sequence comparison between human C2GnT3 (accession #AF132035; SEQ ID NO: 2), human C2GnT2 (formerly designated C2/4GnT; accession #AF038650; SEQ ID NO: 15), human C2GnT1 (formerly designated C2GnT-L; accession #M97347; SEQ ID NO: 13), and human IGnT (accession #Z19550; SEQ ID NO: 17). Introduced gaps are shown as hyphens, and aligned identical residues are boxshaded (black for all sequences, dark grey for three sequences, and light grey for two sequences). The putative transmembrane domains are boxed. The positions of conserved cysteines are indicated by asterisks. One conserved N-glycosylation site is indicated by an open circle. The corresponding nucleotide sequences are SEQ ID NO: 1 (C2GnT3), SEQ ID NO: 14 (C2GnT2), SEQ ID NO: 12 (C2GnT1), and SEQ ID NO: 16 (IGnT).

FIG. 3 depicts Northern blot analyses of healthy human adult and fetal tissues. Panel A: loading pattern for the human mRNA master blot (CLONTECH). Dots in row H contain 100 ng (H1–H7) or 500 ng (H8) of control DNA or RNA. Panel B: autoradiogram of master blot expression analysis using a $^{32}$P-labeled C2GnT3 probe corresponding to the soluble expression fragment of C2GnT3 (base pairs 115–1359). Panel C: A multiple human tissue northern blot (MTN II from Clontech) was probed as described for panel B.

DETAILED DESCRIPTION OF THE INVENTION

Figure 4:
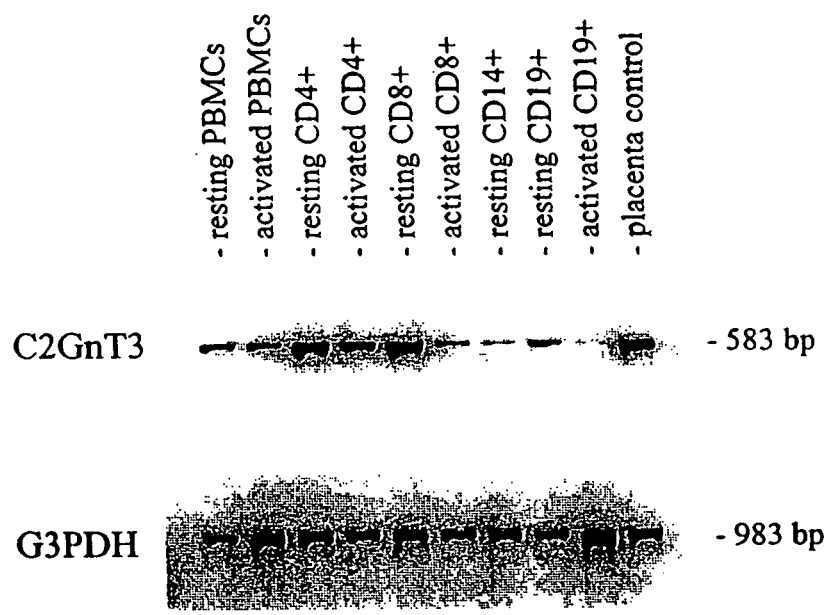
FIG. 4 shows a PCR analysis of C2GnT3 expression in human blood cell fractions. PCR amplificafions with primers specific for human C2GnT3 (C2GnT3) or GAPDH (G3PDH) were performed on a normalized human blood cell cDNA panel (MTC from Clontech) for 31 cycles.

All patent applications, patents, and literature references cited in this specification are hereby incorporated by reference in their entirety. In the case of conflict, the present description, including definitions, is intended to control.

Definitions

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in a mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns, i.e., is free from non-coding sequences, is inserted adjacent to, or within, exogenous (e.g., heterologous) DNA sequences.

3. A plasmid or, more generally, a vector or "expression vector", is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule. Inserted coding sequences do not occur naturally in the organism from which the vector is derived.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate).

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of C2GnT3 are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., a Core-β1,6-N-acetylglucosaminyltransferase and that contributes an N-acetylglucosaminyl moiety for the transferase reaction. For C2GnT3, a donor substrate is UDP-N-acetylglucosamine. An "acceptor substrate" is a molecule, preferably a saccharide or oligosaccharide, that is recognized by, e.g., an N-acetylglucosaminyltransferase and that is the target for the modification catalyzed by the transferase, i.e., receives the N-acetylglucosaminyl moiety. For C2GnT3, acceptor substrates include without limitation oligosaccharides, glycoproteins, O-linked core 1-glycopeptides, and glycosphingolipids comprising the sequences Galβ1–3GalNAc, or GlcNAcβ1–3GalNAc.

9. In accordance with the present invention there may be employed conventional molecular biology, microbiology, and recombinant DNA techniques within the skill of the art. Such techniques are explained fully in the literature. See for example, Sambrook, Fritsch, Maniatis, Molecular Cloning: A Laboratory Manual, Second Edition (1989) Cold Spring Harbor Laboratory Press, Cold Spring Harbor, N.Y); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B.D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984).

10. The terms "sequence similarity" or "sequence identity" refer to the relationship between two or more amino acid or nucleic acid sequences, determined by comparing the sequences, which relationship is generally known as "homology". Identity in the art also means the degree of sequence relatedness between amino acid or nucleic acid sequences, as the case may be, as determined by the match between strings of such sequences. Both identity and similarity can be readily calculated (Computational Molecular Biology, Lesk, A. M., ed., Oxford University Press New York, 1988; Biocomputing: Informatics and Genome Projects, Smith, D. W. ed., Academic Press, New York, 1993; Computer Analysis of Sequence Data, Part I, Griffin, A. M., and Griffin, H. G. eds. Humana Press, New Jersey, 1994; Sequence Analysis in Molecular Biology, von Heinje, G., Academic Press, New York, 1987; and Sequence Analysis Primer, Gribskov, M. and Devereux, S., eds. M. Stockton Press, New York, 1991). While there are a number of existing methods to measure identity and similarity between two amino acid sequences or two nucleic acid sequences, both terms are well known to the skilled artisan (Sequence Analysis in Molecular Biology, von Hinge, G., Academic Press, New York, 1987; Sequence Analysis Primer, Gribskov, M. and Devereux, J., eds. M. Stockton Press, New York, 1991; and Carillo, H., and Lipman, D. SIAM J. Applied Math., 48.1073, 1988). Preferred methods for determining identity are designed to give the largest match between the sequences tested. Methods to determine identity are codified in computer programs. Preferred computer program methods for determining identity and similarity between two sequences include but are not limited to the GCG program package (20), BLASTP, BLASTN, and FASTA (21). Identity or similarity may also be determined using the alignment algorithm of Dayhoff et al. (Methods in Enzymology 91: 524–545 (1983)].

Preferably the nucleic acids of the present invention have substantial sequence identity using the preferred computer programs cited herein, for example greater than 40%, 45%, 50%, 60%, 70%, 75%, 80%, 85%, or 90% identity; more preferably at least 95%, 96%, 97%, 98%, or 99% sequence identity to the sequence shown in SEQ ID NO: 1 and FIG. 1.

Figure 2:
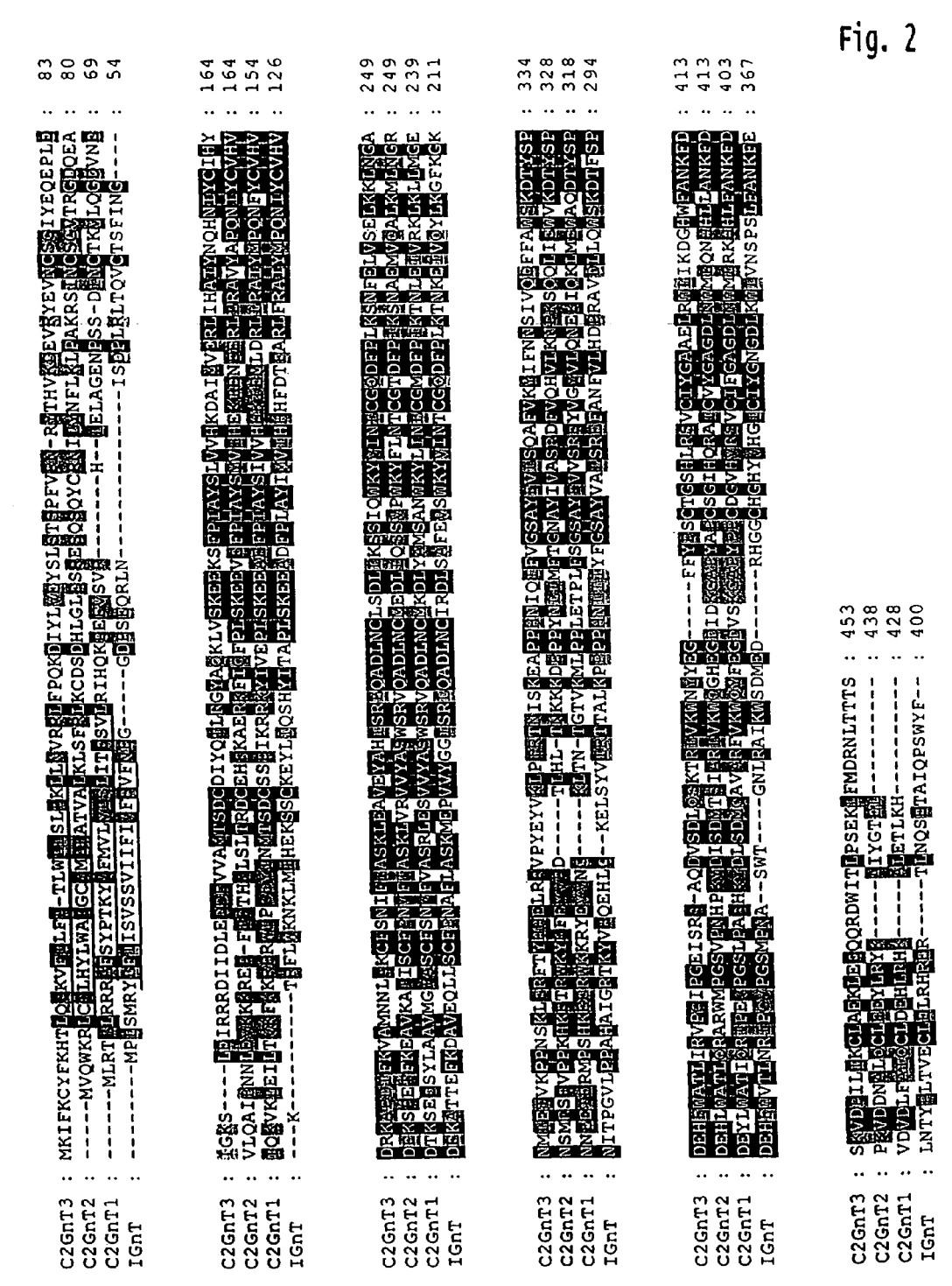

11. The polypeptides of the invention also include homologs of a C2GnT3 polypeptide and/or truncations thereof as described herein. Such homologs include polypeptides whose amino acid sequences are comprised of the amino acid sequences of C2GnT3 polypeptide regions from other species that hybridize under selected hybridization conditions (see discussion of hybridization conditions in particular stringent hybridization conditions herein) with a probe used to obtain a C2GnT3 polypeptide or to SEQ ID NO:1. These homologs will generally have the same regions which are characteristic of a C2GnT3 polypeptide. It is anticipated that a polypeptide comprising an amino acid sequence which has at least 40% identity, at least 45%, or at least 60% similarity, preferably at least 60–65% identity or at least 80–85% similarity, more preferably at least 70–80% identity or at least 90–95% similarity, most preferably at least 95% identity or at least 99% similarity with the amino acid sequence shown in SEQ ID NO: 2 and FIGS. 1 and 2, will be a homolog of a C2GnT3 polypeptide. A percent amino acid sequence similarity or identity is calculated using the methods described herein, preferably the computer programs described herein.

Identificaion and Clining of C2GnT3

The present invention provides the isolated DNA molecules, including genomic DNA and cDNA, encoding the UDP-N-acetylglucosamine: N-acetylgalactosamine β1,6 N-acetylglucosaminyl-transferase 3 (C2GnT3).

C2GnT3 was identified by analysis of genomic survey sequences (GSS), and cloned based on a genomic clone obtained from a human foreskin fibroblast library. The cloning strategy may be briefly summarized as follows: 1) isolation and sequencing of GSS clone CIT-HSP-2288B17.TF (GSS GenBank accession number AQ005888); 2) synthesis of oligonucleotides derived from GSS sequence information, designated TSHC96 and TSHC101; 3) identification, cloning and sequencing of genomic P1 clone GS22597 #844/B1; 4) identification of a novel cDNA sequence corresponding to C2GnT3; 5) confirmatory sequencing of a cDNA clone obtained by reverse-transcription-polymerase chain reaction (RT-PCR) using human thymus poly A-mRNA; 6) construction of expression constructs; 7) expression of the cDNA encoding C2GnT3 in Sf9 (*Spodoptera frugiperda*) cells. More specifically, the isolation of a representative DNA molecule encoding a novel third member of the mammalian UDP-N-acetylglucosamine: β-N-actylgalactosamine β1,6-N-acetylglucosaminyltransferase family involved the following procedures described below.

Identification of DNA Homologous to C2/4GnT (C2GnT2)

Database searches were performed with the coding sequence of the human C2/4GnT (C2GnT2) sequence (13) using the BLASTn and the tBLASTn algorithm with the GSS database at The National Center for Biotechnology Information, USA. The BLASTn algorithm was used to identify clones representing the query gene (identities of ≧95%), whereas tBLASTn was used to identify non-identical, but similar GSS sequences. GSSs with 50–90% nucleotide sequence identity were regarded as different from the query sequence. Two GSS clones with several apparent short sequence motifs and cysteine residues arranged with similar spacing were selected for further sequence analysis.

Cloning of Human C2GnT3

GSS clone CIT-HSP-2288B17.TF (GSS GenBank accession number AQ005888), derived from a putative homologue to C2/4GnT (C2GnT2), was obtained from Research Genetics Inc., USA. Sequencing of this clone revealed a partial open reading frame with significant sequence similarity to C2/4GnT (C2GnT2). The coding region of human C2GnT-L (C2GnT1), C2/4GnT (C2GnT2) and a bovine homologue was previously found to be organized in one exon ((22),(15)). Since the 3' sequence available from the C2GnT3 GSS was incomplete but likely to be located in a single exon, the missing 3' portion of the open reading frame was obtained by sequencing a genomic P1 clone. The P1 clone was obtained from a human foreskin genomic P1 library (DuPont Merck Pharmaceutical Co. Human Foreskin Fibroblast P1 Library) by screening with the primer pair:

```
TSHC96
(5'-GGTTTCACCGTCTCCAACATA-3', SEQ ID NO: 3)
and

TSHC101
(5'-TCGTAAGGCACCTGATACTT-3', SEQ ID NO: 6).
```

One genomic clone for C2GnT3, GS22597 #844/B1 was obtained from Genome Systems Inc. DNA from P1 phage was prepared as recommended by Genome Systems Inc. The entire coding sequence of the C2GnT3 gene was represented in the clone and sequenced in full using automated sequencing (ABI377, Perkin-Elmer). Confirmatory sequencing was performed on a cDNA clone obtained by PCR (30 cycles at 95° C. for 10 sec; 55° C. for 15 sec and 68° C. for 2 min 30 sec) on cDNA from human thymus poly A-mRNA with the sense primer:

```
TSHC99
(5'-CGAGGATCCAGAATGAAGATATTCAAATGTTA-3', SEQ ID
NO: 4),
``` and the anti-sense primer

```
TSHC121
(5'-AGCGAATTCTTACTATCATGATGTGGTAGTG-3', SEQ ID
NO: 9).
```

The composite sequence contained an open reading frame of 1359 base pairs encoding a putative protein of 453 amino acids with type II domain structure predicted by the TMpred-algorithm at the Swiss Institute for Experimental Cancer Research (ISREC).

(http://www.ch.embnet.org/software/TMPRED_form.html).

Expression of C2GnT3

An expression construct designed to encode amino acid residues 39–453 of C2GnT3 was prepared by PCR using P1 DNA, and the primer pair:

```
TSHC100
(5'-CGAGGATCCGCAAAAAGACATTTACTTGGTT-3', SEQ ID
NO: 5)
and

TSHC121
(5'-AGCGAATTCTTACTATCATGATGTGGTAGTG-3', SEQ ID
NO: 9)
``` with BamHI and EcoRI restriction sites, respectively (FIG. 2). The PCR product was cloned between the BamHI and EcoRI sites of pAcGP67A (PharMingen), and the insert was fully sequenced. pAcGP67-C2GnT3-sol was co-transfected with Baculo-Gold™ DNA (PharMingen) as described previously (23). Recombinant Baculovirus was obtained after two successive amplifications in Sf9 cells grown in serum-containing medium, and titers of virus were estimated by titration in 24-well plates with monitoring of enzyme activities. Transfection of Sf9-cells with pAcGP67-C2GnT3-sol resulted in marked increase in GlcNAc-transferase activity compared to uninfected cells or cells infected with a control construct. C2GnT3 showed significant activity with disaccharide derivatives of O-linked core 1 (Galβ1–3GalNAcα1-R). In contrast, no activity was found with core 3 structures (GlcNAcβ1–3GalNAcα1-R), lacto-N-neotetraose as well as GlcNAcβ1–3Gal-Me as acceptor substrates indicating that C2GnT3 has no Core4GnT and IGnT-activity. Additionally, no activity could be detected wih α-D-GalNAc-1- para-nitrophenyl indicating that C2GnT3 does not form core 6 (GlcNAcβ1–6GalNAcα1-R) (Table I). No substrate inhibition of enzyme activity was found at high acceptor concentrations up to 20 mM core 1-para-nitrophenyl. C2GnT3 shows strict donor substrate specificity for UDP-GlcNAc, no activity could be detected with UDP-Gal or UDP-GalNAc (data not shown).

C2GnT1 (FIG. 3C). Multiple transcripts of C2GnT1 have been suggested to be caused by differential usage of polyadenylation signals, which affects the length of the 3' UTR (13).

The C2GnT3 enzyme of the present invention was shown to exhibit O-glycosylation capacity implying that the C2GnT3 gene is vital for correct/full O-glycosylation in vivo as well. A structural defect in the C2GnT3 gene leading to a deficient enzyme or completely defective enzyme would therefore expose a cell or an organism to protein/peptide sequences which were not covered by O-glycosylation as seen in cells or organisms with intact C2GnT3 gene. Described in Example 5 below is a method for scanning the coding exon for potential structural defects. Similar methods could be used for the characterization of defects in the non-coding region of the C2GnT3 gene including the promoter region.

DNA, Vectors, and Host Cells

In practicing the present invention, many conventional techniques in molecular biology, microbiology, recombinant DNA, and immunology, are used. Such techniques are well known and are explained fully in, for example, Sambrook et al., 1989, *Molecular Cloning A Laboratory Manual*, Second Edition, Cold Spring Harbor Laboratory Press, Cold Spring Harbor, N.Y.; *DNA Cloning: A Practical Approach*, Volumes

TABLE I

Substrate specificities of C2GnT3 and C2GnT1

| Substrate | C2GnT3[a] | | C2GnT1 | |
|---|---|---|---|---|
| | 2 mM | 10 mM | 2 mM | 10 mM |
| | nmol/h/mg | | nmol/h/mg | |
| β-D-Gal-(1–3)-α-D-GalNAc | 6.6 | 14.3 | 9.6 | 19.0 |
| β-D-Gal-(1–3)-α-D-GalNAc-1-p-Nph | 18.1 | 26.1 | 16.2 | 23.6 |
| β-D-GlcNAc-(1–3)-α-D-GalNAc-1-p-Nph | <0.1 | <0.1 | <0.1 | <0.1 |
| α-D-GalNAc-1-p-Nph | <0.1 | <0.1 | <0.1 | <0.1 |
| D-GalNAc | <0.1 | <0.1 | <0.1 | <0.1 |
| lacto-N-neo-tetraose | <0.1 | <0.1 | <0.1 | <0.1 |
| β-D-GlcNAc-(1–3)-β-D-Gal-1-Me | <0.1 | <0.1 | <0.1 | <0.1 |

[a] Enzyme sources were partially purified media of infected High Five ™ cells (see "Experimental Procedures"). Background values obtained with uninfected cells or cells infected with an irrelevant construct were subtracted.
[b] Me, methyl; Nph, nitrophenyl.

Controls included the pAcGP67-GalNAc-T3-sol (24). The kinetic properties were determined with partially purified enzymes expressed in High Five™ cells. Partial purification was performed by consecutive chromatography on Amberlite IRA-95, DEAE-Sephacryl and SP-Sepharose essentially as described (25; 25).

Northern Blot analysis of Human Organs

A human RNA master blot containing mRNA from fifty healthy human adult and fetal organs (CLONTECH) and a human multiple tissue northern blot (MTNII from CLONTECH) were probed with a $^{32}$P-labeled probe corresponding to the soluble fragment of C2GnT3 (base pairs 115–1359). The autoradiographic analyses showed expression of C2GnT3 predominantly in lymphoid organs and in organs of the gastrointestinal tract with high transcription levels observed in thymus, and lower levels in PBLs, lymph node, stomach, pancreas and small intestine (FIGS. 3A and 3B). The size of the single transcript was approximately 5.5 kilobases, which correlates to the transcript size of 5.4 kilobases of the biggest of three transcripts of human I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I–IV (Weir and Blackwell eds.).

The invention encompasses isolated nucleic acid fragments comprising all or part of the nucleic acid sequence disclosed herein as set forth in FIG. 1. The fragments are at least about 8 nucleotides in length, preferably at least about 12 nucleotides in length, and most preferably at least about 15–20 nucleotides in length. The invention further encompasses isolated nucleic acids comprising sequences that are hybridizable under stringency conditions of 2×SSC, 55° C., to the sequence set forth in FIG. 1; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including transcriptional control elements such as promoters, enhancers, and response elements, or other sequences such as signal sequences, polyadenylation sequences, introns, 5'- and 3'- noncoding regions, and the like. Preferably, although not necessarily, any two nucleotide sequences to be expressed as a fusion polypeptide are inserted in-frame. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences as set forth in FIG. 1 or sequence-conservative or function-conservative variants thereof, or a complement thereof, and that has been labelled as described above.

The invention also provides nucleic acid vectors comprising the disclosed sequence or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells included bacteria, archaebacteria, fungi, especially yeast, and plant and animal cells, especially mammalian cells. Also included are avian and insect cells. Of particular interest are *Saccharomyces cerevisiae, Schizosaccharomyces pombe, Pichia pastoris, Hansenula polymorpha, Neurospora* spec., SF9 cells, C129 cells, 293 cells, and CHO cells, COS cells, HeLa cells, and immortalized mammalian myeloid and lymphoid cell lines. Preferred replication systems include M13, ColE1, 2µ, ARS, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced C2GnT3 derived peptides and polypeptides.

Advantageously, vectors may also include a transcription regulatory element (i.e., a promoter) operably linked to the C2GnT3 coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GAL1) promoter, galactoepimerase (GAL10) promoter, metallothioneine (CUP) promoter and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use, for example, as probes for the detection of C2GnT3 in other species or related organisms and as templates for the recombinant production of peptides or polypeptides. These and other embodiments of the present invention are described in more detail below.

Polypeptides and Antibodies

The present invention encompasses isolated peptides and polypeptides encoded by the disclosed cDNA sequence. Peptides are preferably at least five residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of (26), the method of (27), or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well known in the art, including, without limitation, preparative discontiuous gel elctrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, an affinity ligand, reactive group, and/or a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that specifically recognize immunogenic components derived from C2GnT3. Such antibodies can be used as reagents for detection and purification of C2GnT3.

C2GnT3 specific antibodies according to the present invention include polyclonal and monoclonal antibodies. The antibodies may be elicited in an animal host by immunization with C2GnT3 components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well known in the art. For example, techniques for producing and processing polyclonal antisera are disclosed in Mayer and Walker, 1987, *Immunochemical Methods in Cell and Molecular Biology*, (Academic Press, London).

The antibodies of this invention can be purified by standard methods, including but not limited to preparative disc-gel elctrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification*, 1989, Amicon Division, W. R. Grace & Co. General protein purification methods are described in *Protein Purification: Principles and Practice*, R. K. Scopes, Ed., 1987, Springer-Verlag, New York, NY.

Anti C2GnT3 antibodies, whether unlabeled or labeled by standard methods, can be used as the basis for immunoassays. The particular label used will depend upon the type of immunoassay used. Examples of labels that can be used include, but are not limited to, radiolabels such as $^{32}P$, $^{125}I$, $^3H$ and $^{14}C$; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzandine and the like may be used to tag the antibodies with fluorescent, chemiluminescent or enzyme labels. The general methods involved are well known in the art and are described in, e.g., Chan (Ed.), 1987, *Immunoassay: A Practical Guide*, Academic Press, Inc., Orlando, Fla.

Applications of the Nucleic Acid Molecules, Polypeptides, and Antibodies of the Invention The nucleic acid molecules, C2GnT3 polypeptide, and antibodies of the invention may be used in the prognostic and diagnostic evaluation of conditions associated with altered expression or activity of a polypeptide of the invention or conditions requiring modulation of a nucleic acid or polypeptide of the invention including thymus-related disorders and proliferative disorders (e.g. cancer), and the identification of subjects with a predisposition to such conditions (See below). Methods for detecting nucleic acid molecules and polypeptides of the invention can be used to monitor such conditions by detecting and localizing the polypeptides and nucleic acids. It would also be apparent to one skilled in the art that the methods described herein may be used to study the developmental expression of the polypeptides of the invention and, accordingly, will provide further insight into the role of the polypeptides. The applications of the present invention also include methods for the identification of substances or compounds that modulate the biological activity of a polypeptide of the invention (See below). The substances, compounds, antibodies etc., may be used for the treatment of conditions requiring modulation of polypeptides of the invention (See below).

Diagnostic Methods

A variety of methods can be employed for the diagnostic and prognostic evaluation of conditions requiring modulation of a nucleic acid or polypeptide of the invention (e.g. thymus-related disorders, and cancer), and the identification of subjects with a predisposition to such conditions.

Such methods may, for example, utilize nucleic acids of the invention, and fragments thereof, and antibodies directed against polypeptides of the invention, including peptide fragments. In particular, the nucleic acids and antibodies may be used, for example, for: (1) the detection of the presence of C2GnT3 mutations, or the detection of either over- or under-expression of C2GnT3 mRNA relative to a non-disorder state or the qualitative or quantitative detection of alternatively spliced forms of C2GnT3 transcripts which may correlate with certain conditions or susceptibility toward such conditions; or (2) the detection of either an over- or an under-abundance of a polypeptide of the invention relative to a non-disorder state or the presence Of a modified (e.g., less than full length) polypeptide of the invention which correlates with a disorder state, or a progression toward a disorder state.

The methods described herein may be performed by utilizing pre-packaged diagnostic kits comprising at least one specific nucleic acid or antibody described herein, which may be conveniently used, e.g., in clinical settings, to screen and diagnose patients and to screen and identify those individuals exhibiting a predisposition to developing a disorder.

Nucleic acid-based detection techniques and peptide detection techniques are described below. The samples that may be analyzed using the methods of the invention include those that are known or suspected to express C2GnT3 nucleic acids or contain a polypeptide of the invention. The methods may be performed on biological samples including but not limited to cells, lysates of cells which have been incubated in cell culture, chromosomes isolated from a cell (e.g. a spread of metaphase chromosomes), genomic DNA (in solutions or bound to a solid support such as for Southern analysis), RNA (in solution or bound to a solid support such as for northern analysis), cDNA (in solution or bound to a solid support), an extract from cells or a tissue, and biological fluids such as serum, urine, blood, and CSF. The samples may be derived from a patient or a culture.

Methods for Detection of Nucleic Acid Molecules of the Invention

The nucleic acid molecules of the invention allow those skilled in the art to construct nucleotide probes for use in the detection of nucleic acid sequences of the invention in biological materials. Suitable probes include nucleic acid molecules based on nucleic acid sequences encoding at least 5 sequential amino acids from regions of the C2GnT3 polypeptide (see SEQ ID NO: 1), preferably they comprise 15 to 50 nucleotides, more preferably 15 to 40 nucleotides, most preferably 15–30 nucleotides. A nucleotide probe may be labelled with a detectable substance such as a radioactive label that provides for an adequate signal and has sufficient half-life such as $^{32}P$, $^{3}H$, $^{14}C$ or the like. Other detectable substances that may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect C2GnT3 genes, preferably in human cells. The nucleotide probes may also be used for example in the diagnosis or prognosis of conditions such as thymus-related disorders and cancer, and in monitoring the progression of these conditions, or monitoring a therapeutic treatment.

The probe may be used in hybridisation techniques to detect a C2GnT3 gene. The technique generally involves contacting and incubating nucleic acids (e.g. recombinant DNA molecules, cloned genes) obtained from a sample from a patient or other cellular source with a probe of the present invention under conditions favourable for the specific annealing of the probes to complementary sequences in the nucleic acids. Alter incubation, the non-annealed nucleic acids are removed, and the presence of nucleic acids that have hybridized to the probe if any are detected.

The detection of nucleic acid molecules of the invention may involve the amplification of specific gene sequences using an amplification method (e.g. PCR), followed by the analysis of the amplified molecules using techniques known to those skilled in the art. Suitable primers can be routinely designed by one of skill in the art. For example, primers may be designed using commercially available software, such as OLIGO 4.06 Primer Analysis software (National Biosciences, Plymouth, Minn.) or another appropriate program, to be about 22 to 30 nucleotides in length, to have a GC content of about 50% or more, and to anneal to the template at temperatures of about 60° C. to 72° C.

Genomic DNA may be used in hybridization or amplification assays of biological samples to detect abnormalities involving C2GnT3 nucleic acid structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a C2GnT3 gene. The polymorphisms may be used to identify individuals in families that are likely to carry mutations. If a polymorphism exhibits linkage disequilibrium with mutations in the G2GnT3 gene, it can also be used to screen for individuals in the general population likely to carry mutations. Polymorphisms which may be used include restriction fragment length polymorphisms (RFLPs), single-nucleotide polymorphisms (SNP), and simple sequence repeat polymorphisms (SSLPs).

A probe or primer of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of C2GnT3 expression. For example RNA may be isolated from a cell type or tissue known to express C2GnT3 and tested utilizing the hybridization (e.g. standard Northern analyses) or PCR techniques referred to herein. The techniques may be used to detect differences in transcript size that may be doe to normal or abnormal alternative splicing. The techniques may be used to detect quantitative differences between levels of full length and/or alternatively splice transcripts detected in normal individuals relative to those individuals exhibiting symptoms of a disease.

The primers and probes may be used in the above described methods in situ i.e directly on tissue sections (fixed and/or frozen) of patient tissue obtained from biopsies or resections.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to identify predisposition to a disorder, to treat a disorder, to diagnose a disorder, and to develop and monitor the activities of therapeutic agents.

The preparation, use, and analysis of micro arrays are well known to a person skilled in the art. (see, for example, Brennan, T. M., et al. (1995), U.S. Pat. No. 5,474,796; Schena et al. (1996), Proc. Natl. Acad. Sci. 93:10614–10619; Baldeschweiler et al. (1995), PCT Application WO95/251116; Shalon, D., et al. (1995), PCT application WO95/35505; Heller, R. A., et al. (1997), Proc. Natl. Acad. Sci. 94:2150–2155; and Heller, M. J., et al. (1997), U.S. Pat. No. 5,605,662.)

Methods for Detecting Polypeptides

Antibodies specifically reactive with a C2GnT3 Polypeptide, or derivatives, such as enzyme conjugates or labeled derivatives, may be used to detect C2GnT3 polypeptides in various biological materials. They may be used as diagnostic or prognostic reagents and they may be used to detect abnormalities in the level of C2GnT3 polypeptides, expression, or abnormalities in the structure, and/or temporal, tissue, cellular, or subcellular location of the polypeptides. Antibodies may also be used to screen potentially therapeutic compounds in vitro to determine their effects on a condition such as a thymus-related disorder or cancer. In vitro immunoassays may also be used to assess or monitor the efficacy of particular therapies. Preferably, antibodies for use in a detection assay have a dissociation constant lower than 1 µM, even more preferably lower than or about 10 nM.

The antibodies of the invention may also be used in vitro to determine the level of C2GnT3 polypeptide expression in cells genetically engineered to produce a C2GnT3 polypeptide. The antibodies may be used to detect and quantify polypeptides of the invention in a sample in order to determine their role in particular cellular events or pathological states, and to diagnose and treat such pathological states.

In particular, the antibodies of the invention may be used in immuno-histochemical analyses, for example, at the cellular and sub-subcellular level, to detect a polypeptide of the invention, to localize it to particular cells and tissues, and to specific subcellular locations, and to quantitate the level of expression.

The antibodies may be used in any known immunoassays that rely on the binding interaction>> between an antigenic determinant of a polypeptide of the invention, and the antibodies. Examples of such assays are radio immunoassays, enzyme immunoassays (e.g. ELISA), immunofluorescence, immunoprecipitation, latex agglutination, hemagglutination, and histochemical tests, Cytochemical techniques known in the art for localizing antigens using light and electron microscopy may be used to detect a polypeptide of the invention. Generally, an antibody of the invention may be labelled with a detectable substance and a polypeptide may be localised in tissues and cells based upon the presence of the detectable substance. Various methods of labelling polypeptides are known in the art and may be used. Examples of detectable substances include, but are not limited to, the following: radioisotopes (e.g., $^3$H, $^{14}$C, $^{35}$S, $^{125}$I, 131I), fluorescent labels (e.g., FITC, Rhodamine, lanthanide phosphors), luminescent labels such as luminol, enzymatic labels (e.g., horseradish peroxidase, β-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies, etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against a polypeptide of the invention. By way of example, if the antibody having specificity against a polypeptide of the invention is a rabbit IgG antibody, the second antibody may be goat anti-rabbit gamma-globulin labelled with a detectable substance as described herein.

Where a radioactive label is used as a detectable substance, a polypeptide of the invention may be localized by radioautography. The results of radioautography may be quantitated by determining the density of particles in the radioautographs by various optical methods, or by counting the grains.

A polypeptide of the invention may also be detected by assaying for C2GnT3 activity as described herein. For example, a sample may be reacted with an acceptor substrate and a donor substrate under conditions where a C2GnT3 polypeptide is capable of transferring the donor substrate to the acceptor substrate to produce a donor substrate-acceptor substrate complex.

Methods for Identifying or Evaluating Substances/Compounds

The methods described herein are designed to identify substances and compounds that modulate the expression or biological activity of a C2GnT3 polypeptide including substances that interfere with or enhance the expression or activity of a C2GnT3 polypeptide.

Substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], polypeptides, nucleic acids, carbohydrates, and small organic or inorganic molecules. A substance or compound may be an endogenous physiological compound or it may be a natural or synthetic compound.

Modulation of a C2GnT3 polypeptide can be evaluated, for instance, by evaluating the inhibitory/stimulatory effect of an agent on C2GnT3 biological activity in comparison to a control or reference. The control or reference may be, e.g., a predetermined reference value, or may be evaluated experimentally. For example, in a cell-based assay where a host cell expressing recombinant C2GnT3 is incubated in a medium containing a potential modulating agent, a control or reference may be, e.g., a host cell incubated with an agent having a known effect on C2GnT3 expression/activity, a host cell incubated in the same medium without any agent, a host cell transfected with a "mock" vector not expressing any C2GnT3 polypeptide, or any other suitable control or reference. In a cell-free assay where C2GnT3 polypeptide is incubated in a medium containing a potential modulating agent, a control or reference may be, for example, medium not containing C2GnT3 polypeptide, medium not containing any agent, medium containing a reference polypeptide or agent, or any other suitable control or reference.

Substances which modulate a C2GnT3 polypeptide can be identified based on their ability to associate with a C2GnT3 polypeptide. Therefore, the invention also provides methods for identifying substances that associate with a C2GnT3 polypeptide. Substances identified using the methods of the invention may be isolated, cloned and sequenced using conventional techniques. A substance that associates with a polypeptide of the invention may be an agonist or antagonist of the biological or immunological activity of a polypeptide of the invention.

The term "agonist" refers to a molecule that increases the amount of, or prolongs the duration of, the activity of the polypeptide. The term "antagonist" refers to a molecule which decreases the biological or immunological activity of the polypeptide. Agonists and antagonists may include proteins, nucleic acids, carbohydrates, or any other molecules that associate with a polypeptide of the invention.

Substances which can associate with a C2GnT3 polypeptide may be identified by reacting a C2GnT3 polypeptide with a test substance which potentially associates with a C2GnT3 polypeptide, under conditions which permit the association, and removing and/or detecting the associated C2GnT3 polypeptide and substance. Substance-polypeptide complexes, free substance, or non-complexed polypeptides may be assayed. Conditions which permit the formation of substance-polypeptide complexes may be selected having regard to factors such as the nature and amounts of the substance and the polypeptide.

The substance-polypeptide complex, free substance or non-complexes polypeptides may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against a polypeptide of the invention or the substance, or labelled polypeptide, or a labelled substance may be utilized. The antibodies, polypeptides, or substances may be labelled with a detectable substance as described above.

A C2GnT3 polypeptide, or the substance used in the method of the invention may be insolubilized. For example, a polypeptide, or substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized polypeptide or substance may be prepared by reacting the material with a suitable insoluble carrier using known chemical or physical methods, for example, cyanogen bromide coupling.

The invention also contemplates a method for evaluating a compound for its ability to modulate the biological activity of a polypeptide of the invention, by assaying for an agonist or antagonist (i.e. enhancer or inhibitor) of the association of the polypeptide with a substance which interacts with the polypeptide (e.g. donor or acceptor substrates or parts thereof). The basic method for evaluating if a compound is an agonist or antagonist of the association of a polypeptide of the invention and a substance that associates with the polypeptide is to prepare a reaction mixture containing the polypeptide and the substance under conditions which permit the formation of substance-polypeptide complexes, in the presence of a test compound. The test compound may be initially added to the mixture, or may be added subsequent to the addition of the polypeptide and substance. Control reaction mixtures without the test compound or with a placebo are also prepared. The formation of complexes is detected and the formation of complexes in the control reaction but not in the reaction mixture indicates that the test compound interferes with the interaction of the polypeptide and substance. The reactions may be carried out in the liquid phase or the polypeptide, substance, or test compound may be immobilized as described herein. The agent can be selected from compounds, compositions, antibodies or antibody fragments, antisense sequences and ribozyme nucleotide sequences for C2GnT3 polypeptide.

It will be understood that the agonists and antagonists i.e. inhibitors and enhancers, that can be assayed using the methods of the invention may act on one or more of the interaction sites an the polypeptide or substance including agonist binding sites, competitive antagonist binding cites, non-competitive antagonist binding sites or allosteric sites.

The invention also makes it possible to screen for antagonists that inhibit the effects of an agonist of the interaction of a polypeptide of the invention with a substance which is capable of associating with the polypeptide. Thus, the invention may be used to assay for a compound that competes for the same interacting site of a polypeptide of the invention.

Substances that modulate a C2GnT3 polypeptide of the invention can be identified based on their ability to interfere with or enhance the activity of a C2GnT3 polypeptide. Therefore, the invention provides a method for evaluating a compound for its ability to modulate the activity of a C2GnT3 polypeptide comprising (a) reacting an acceptor substrate and a donor substrate for a C2GnT3 polypeptide in the presence of a test substance; (b) measuring the amount of donor substrate transferred to acceptor substrate, and (c) carrying out steps (a) and (b) in the absence of the test substance to determine if the substance interferes with or enhances transfer of the sugar donor to the acceptor by the C2GnT3 polypeptide.

Suitable acceptor substrate for use in the methods of the invention are a saccharide, oligosaccharides, polysaccharides, polypeptides, glycopolypeptides, or glycolipids which are either synthetic with linkers at the reducing end or naturally occuring structures, for example, asialo-agalacto-fetuin glycopeptide. Acceptors will generally comprise β-D-galactosyl-1,3-N-acetyl-D-galactosaminyl-.

The donor substrate may be a nucleotide sugar, dolichol-phosphate-sugar or dolichol-pyrophosphate-oligosaccharide, for example, uridine diphospho-N-acetylglucosamine (UDP-GlcNAc), or derivatives or analogs thereof. The C2GnT3 polypeptide may be obtained from natural sources or produced used recombinant methods as described herein.

The acceptor or donor substrates may be labeled with a detectable substance as described herein, and the interaction of the polypeptide of the invention with the acceptor and donor will give rise to a detectable change. The detectable change may be colorimetric, photometric, radiometric, potentiometric, etc. The activity of C2GnT3 polypeptide of the invention may also be determined using methods based on HPLC (Koenderman et al., FEBS Lett. 222: 42, 1987) or methods employed synthetic oligosaccharide acceptors attached to hydrophobic aglycones (Palcic et al Glycoconjugate 5:49, 1988; and Pierce et al, Biochem. Biophys. Res. Comm. 146: 679, 1987).

The C2GnT3 polypeptide is reacted with the acceptor and donor substrates at a pH and temperature effective for the polypeptide to transfer the donor to the acceptor, and where one of the components is labeled, to produce a detectable change. It is preferred to use a buffer with the acceptor and donor to maintain the pH within the pH range effective for the polypeptides. The buffer, acceptor and donor may be used as an assay composition. Other compounds such as EDTA and detergents may be added to the assay composition.

The reagents suitable for applying the methods of the invention to evaluate compounds that modulate a C2GnT3 polypeptide may be packaged into convenient kits providing the necessary materials packaged into suitable containers. The kits may also include suitable supports useful in performing the methods of the invention.

Substances that modulate a C2GnT3 polypeptide can also be identified by treating immortalized cells which express the polypeptide with a test substance, and comparing the morphology of the cells with the morphology of the cells in the absence of the substance and/or with immortalized cells which do not express the polypeptide. Examples of immortalized cells that can be used include lung epithelial cell lines such as MvlLu or HEK293 (human embryonal kidney) transfected with a vector containing a nucleic acid of the invention. In the absence of an inhibitor the cells show signs of morphologic transformation (e.g. fibroblastic morphology, spindle shape and pile up; the cells are less adhesive to substratum; there is less cell to cell contact in monolayer culture; there is reduced growth-factor requirements for survival and proliferation; the cells grow in soft-agar of other semi-solid medium; there is a lack of contact inhibition and increased apoptosis in low-serum high density cultures; there is enhanced cell motility, and there is invasion into extracellular matrix and secretion of proteases). Substances that inhibit one or more phenotypes may be considered an inhibitor.

A substance that inhibits a C2GnT3 polypeptide may be identified by treating a cell which expresses the polypeptide with a test substance, and assaying for complex core 2-based O-linked structures (e.g. repeating Gal[β]1–4GlcNAc[β]) associated with the cell. The complex core 2-based O-linked structures can be assayed using a. substance that binds to the structures (e.g. antibodies). Cells that have not been treated with the substance or which do not express the polypeptide may be employed as controls.

Substances which inhibit transcription or translation of a C2GnT3 gene may be identified by transfecting a cell with an expression vector comprising a recombinant molecule of the invention, including a reporter gene, in the presence of a test substance and comparing the level of expression of the C2GnT3 polypeptide, or the expression of the polypeptide encoded by the reporter gene with a control cell transfected with the nucleic acid molecule in the absence of the substance. The method can be used to identify transcription and translation inhibitors of a C2GnT3 gene.

Compositions and Treatments

The substances or compounds identified by the methods described herein, polypeptides, nucleic acid molecules, and antibodies of the invention may be used for modulating the biological activity of a C2GnT3 polypeptide, and they may be used in the treatment of conditions mediated by a C2GnT3 polypeptide. In particular, they may be used to T-cell development and lymphocyte homing and they may be used in the prevention and treatment of thymus-related disorders.

Therefore, the present invention may be useful for diagnosis or treatment of various thymus-related disorders in mammals, preferably humans. Such disorders include the following: tumors and cancers, hypoactivity, hyperactivity, atrophy, enlargement of the thymus, and the like. Other disorders include disregulation of T-lymphocyte selection or activity and would include but not be limited to disorders involving autoimmunity, arthritis, leukemias, lymphomas, immunosuppression, sepsis, wound healing, acute and chronic in action, cell mediated immunity, humor immunity, TH1/TH2 imbalance, and the like.

The substances or compounds identified by the methods described herein, antibodies, and polypeptides, and nucleic acid molecules of the invention may be useful in the prevention and treatment of tumors. Tumor metastasis may be inhibited or prevented by inhibiting the adhesion of circulating cancer cells. The substances, compounds, etc. of the invention may be especially useful in the treatment of various forms of neoplasia such as leukemias, lymphomas, melanomas, adenomas, sarcomas, and carcinomas of solid tissues in patients. In particular the composition may be used for treating malignant melanoma, pancreatic cancer, cervico-uterine cancer, cancer of the liver, kidney, stomach, lung, rectum, breast, bowel, gastric, thyroid, neck, cervix, salivary gland, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The substances etc. are particularly useful in the prevention and treatment of tumors of the immune system and thymus and the metastases derived from these tumors.

A substance or compound identified in accordance with the methods described herein, antibodies, polypeptides, or nucleic acid molecules of the invention may be used to modulate T-cell activation and immunodeficiency due to the Wiskott-Aldrich syndrome or AIDS, or to stimulate hematopoietic progenitor cell growth, and/or confer protection against chemotherapy and radiation therapy in a subject.

Accordingly, the substances, antibodies, and compounds may be formulated into pharmaceutical compositions for administration to subjects in a biologically compatible form suitable for administration in vivo. By biologically compatible form suitable for administration in vivo is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administeted daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound.

The compositions described herein can be prepared by methods known per se for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

After pharmaceutical compositions have been prepared, they can be placed in an appropriate container and labeled for treatment of an indicated condition. For administration of an inhibitor of a polypeptide of the invention, such labeling would include amount, frequency, and method of administration.

The nucleic acids encoding C2GnT3 polypeptides or any fragment thereof, or antisense sequences may be used for therapeutic purposes. Antisense to a nucleic acid molecule encoding a polypeptide of the invention may be med in situations to block the synthesis of the polypeptide. In particular, cells may be transformed with sequences complementary to nucleic acid molecules encoding C2GnT3 polypeptide. Thus, antisense sequences may be used to modulate C2GnT3 activity or to achieve regulation of gene function. Sense or antisense oligomers or larger fragments, can be designed from various locations along the coding or regulatory regions of sequences encoding a polypeptide of the invention.

Expression vectors may be derived from retroviruses, adenoviruses, herpes or vaccinia viruses or from various bacterial plasmids for delivery of nucleic acid sequences to the target organ, tissue, or cells. Vectors that express antisense nucleic acid sequences of C2GnT3 polypeptide can be constructed using techniques well known to those skilled in the art (see for example, Sambrook, Fritsch, Maniatis, Molecular Cloning, A Laboratory Manual, Second Edition (1989) Cold Spring Harbor Laboratory Press, Cold Spring Harbor, N.Y).

Genes encoding C2CnT3 polypeptide can be turned off by transforming a cell or tissue with expression vectors that express high levels of a nucleic acid molecule or fragment thereof which encodes a polypeptide of the invention. Such constructs may be used to introduce untranslatable sense or antisense sequences into a cell. Even if they do not integrate into the DNA, the vectors may continue to transcribe RNA molecules until all copies are disabled by endogenous nucleases. Transient expression may last for extended periods of time (e.g. a month or more) with a non-replicating vector or if appropriate replication elements are part of the vector system.

Modification of gene expression may be achieved by designing antisense molecules, DNA, RNA, or PNA, to the control regions of a C2GnT3 polypeptide gene i.e. the promoters, enhancers, and introns. Preferably the antisense molecules are oligonucleotides derived from the transcription initiation site (e.g. between positions −10 and +10 from the start site). Inhibition can also be achieved by using triple-helix base-pairing techniques. Triple helix pairing causes inhibition of the ability of the double helix to open sufficiently for the binding of polymerases, transcription factors, or regulatory molecules (see Gee J. E. et al (1994) In: Huber, B. E. and B. I. Carr, Molecular and Immunologic Approaches, Futura Publishing Co., Mt. Kisco, N.Y.).

Ribozymes, enzymatic RNA molecules, may be used to catalyze the specific cleavage of RNA. Ribozyme action involves sequence-specific hybridization of the ribozyme molecule to complementary target RNA, followed by endonucleolytic cleavage. For example, hammerhead motif ribozyme molecules may be engineered that can specifically and efficiently catalyze endonucleolytic cleavage of sequences encoding a polypeptide of the invention.

Specific ribosome cleavage sites within any RNA target may be initially identified by scanning the target molecule for ribozyme cleavage sites which include the following sequences: GUA, GUU, and GUC. Short RNA sequences of between 15 and 20 ribonucleotides corresponding to the region of the cleavage site of the target gene may be evaluated for secondary structural features which may render the oligonucleotide inoperable. The suitability of candidate targets may be evaluated by testing accessibility to hybridization with complementary oligonucleotides using ribonuclease protection assays.

Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred.

The invention also provides methods for studying the function of a C2GnT3 polypeptide. Cells, tissues, and non-human animals lacking in C2GnT3 expression or partially lacking in C2GnT3 expression may be developed using recombinant expression vectors of the invention having specific deletion or insertion mutations in a C2GnT3 gene. A recombinant expression vector may be used to inactivate or alter the endogenous gene by homologous recombination, and thereby create a C2GnT3 deficient cell, tissue or animal.

Null alleles may be generated in cells, such as embryonic stem cells by deletion mutation. A recombinant C2GnT3 gene may also be engineered to contain an insertion mutation which inactivates C2GnT3. Such a construct may then be introduced into a cell, such as an embryonic stem cell, by a technique such as transfection, electroporation, injection etc. Cells lacking an intact C2GnT3 gene may then be identified, for example by Southern blotting, Northern Blotting or by assaying for expression of a polypeptide of the invention using the methods described herein. Such cells may then be used to generate transgenic non-human animals deficient in C2GnT3. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on C2GnT3 expression.

The invention thus provides a transgenic non-human mammal all of whose germ cells and somatic cells contain a recombinant expression vector that inactivates or alters a gene encoding a C2GnT3 polypeptide. Further the invention provides a transgenic non-human mammal, which does not express a C2GnT3 polypeptide of the invention.

A transgenic non-human animal includes but is not limited to mouse, rat, rabbit, sheep, hamster, guinea pig, micropig, pig, dog, cat, goat, and non-human primate, preferably mouse.

The invention also provides a transgenic non-human animal assay system which provides a model system for testing for an agent that reduces or inhibits a pathology associated with a C2GnT3 polypeptide comprising: (a) administering the agent to a transgenic non-human animal of the invention; and (b) determining whether said agent reduces or inhibits the pathology in the transgenic non-human animal relative to a transgenic non-human animal of step (a) to which the agent has not been administered.

The agent may be useful to treat the disorders and conditions discussed herein. The agents may also be incorporated in a pharmaceutical composition as described herein.

A polypeptide of the invention may be used to support the survival, growth, migration, and/or differentiation of cells expressing the polypeptide. Thus, a polypeptide of the invention may be used as a supplement to support, for example cells in culture.

Methods to Prepare Oligosaccharides

The invention relates to a method for preparing an oligosaccharide comprising contacting a reaction mixture comprising an activated donor substrate e.g. GlcNAc, and an acceptor substrate in the presence of a polypeptide of the invention.

Examples of acceptor substrates for use in the method for preparing an oligosaccharide are a saccharide, oligosaccharides, polysaccharides, glycopeptides, glycopolypeptides, or glycolipids which are either synthetic with linkers at the reducing end or naturally occurring structures, for example, asialo-agalacto-fetuin glycopeptide. The activated donor substrate is preferably GlcNAc which may be part of a nucleotide-sugar, a dolichol-phosphate-sugar, or dolichol-pyrophosphate-oligosaccharide.

In an embodiment of the invention, the oligosaccharides are prepared on a carrier that is non-toxic to a mammal, in particular a human such as a lipid isoprenoid or polyisoprenoid alcohol. An example of a suitable carrier is dolichol phosphate. The oligosaccharide may be attached to a carrier via a labile bond allowing for chemical removal of the oligosaccharide from the lipid carrier. In the alternative, the oligosaccharide transferase may be used to transfer the oligosaccharide from a lipid carrier to a polypeptide.

The following examples are intended to further illustrate the invention without limiting its scope.

EXAMPLE 1

A: Identification of cDNA Homologous to C2GnT3 by Analysis of GSS Database Sequence Information.

Database searches were performed with the coding sequence of the human C2/4GnT (C2GnT2) sequence using the BLASTn and tBLASTn algorithms against the GSS database at The National Center for Biotechnology Information, USA. The BLASTn algorithm was used to identify GSSs representing the query gene (identities of $\geq 95\%$), whereas tBLASTn was used to identify non-identical, but similar GSS sequences. GSSs with 50–90% nucleotide sequence identity were regarded as different from the query sequence. Composites of the sequence information for two GSSs were compiled and analysed for sequence similarity to human C2/4GnT (C2GnT2).

B: Cloning and Sequencing of C2GnT3

A GSS clone CIT-HSP-2288B17.TF (GSS GenBank accession number AQ005888), derived from a putative homologue to C2/4GnT (C2GnT2), was obtained from Research Genetics Inc., USA. Sequencing of this clone revealed a partial open reading frame with significant sequence similarity to C2/4GnT (C2GnT2). The coding region of human C2GnT-L (C2GnT1), C2/4GnT (C2GnT2) and a bovine homologue was previously found to be organized in one exon ((22),(15)). Since the 3' sequence available from the C2GnT3 GSS was incomplete but likely to be located in the single exon, the missing 3' portion of the open reading frame was obtained by sequencing a genomic P1 clone. The P1 clone was obtained from a human foreskin genomic P1 library (DuPont Merck Pharmaceutical Co. Human Foreskin Fibroblast P1 Library) by screening with the primer pair:

```
TSHC96
(5'-GGTTTCACCGTCTCCAACATA-3', SEQ ID NO: 3)
and
TSHC101
(5'-TCGTAAGGCACCTGATACTT-3', SEQ ID NO: 6).
```

One genomic clone for C2GnT3, GS22597 #844/B1 was obtained from Genome Systems Inc., USA. DNA from P1 phage was prepared as recommended by Genome Systems Inc. The entire coding sequence of the C2GnT3 gene was represented in the clone and sequenced in full using automated sequencing (ABI377, Perkin-Elmer). Confirmatory sequencing was performed on a cDNA clone obtained by PCR (30 cycles at 95° C. for 10 sec; 55° C. for 15 sec and 68° C. for 2 min 30 sec) on cDNA from human thymus poly A-mRNA with the sense primer:

```
TSHC99
(5'-CGAGGATCCAGAATGAAGATATTCAAATGTTA-3', SEQ ID
NO: 4),
``` and the anti-sense primer:

```
TSHC121
(5'-AGCGAATTCTTACTATCATGATGTGGTAGTG-3', SEQ ID
NO: 9).
```

The composite sequence contained an open reading frame of 1359 base pairs encoding a putative protein of 453 amino acids with type II domain structure predicted by the TMpred-algorithm at the Swiss Institute for Experimental Cancer Research (ISREC).(http://www.ch.embnet.org/software/TMPRED_form.html).

EXAMPLE 2

A: Expression of C2GnT3 in Sf9 Cells

An expression vector construct designed to encode amino acid residues 39–453 of C2GnT3 was prepared by PCR using P1 DNA, and the primer pair:

```
TSHC100
(5'-CGAGGATCCGCAAAAAGACATTTACTTGGTT-3', SEQ ID
NO: 5)
and

TSHC121
(5'-AGCGAATTCTTACTATCATGATGTGGTAGTG-3', SEQ ID
NO: 9)
``` with BamH1 and EcoRI restriction sites, respectively (FIG. 2). The PCR product was cloned between the BamHI and EcoRI sites of pAcGP67A (PharMingen), and the insert was fully sequenced. pAcGP67-C2GnT3-sol was co-transfected with Baculo-Gold™ DNA (PharMingen) as described previously (23). Recombinant Baculo-viruses were obtained after two successive amplifications in Sf9 cells grown in serum-containing medium, and titers of virus were estimated by titration in 24-well plates with monitoring of enzyme activities. Transfection of Sf9-cells with pAcGP67-C2GnT3-sol resulted in marked increase in GlcNAc-transferase activity compared to uninfected cells or cells infected with a control construct.

B: Analysis of C2GnT3 Activity

Standard assays were performed using culture supernatant from infected cells in 50 µl reaction mixtures containing 100 mM MES (pH 6.5), 0.1% Nonidet P-40, 150 µM UDP-[$^{14}$C]-GlcNAc (2,000 cpm/nmol) (Amersham Pharmacia Biotech), and the indicated concentrations of acceptor substrates (Sigma and Toronto Research Laboratories Ltd., see Table I for structures). Reaction products were quantified by chromatography on Dowex AG1-X8.

EXAMPLE 3

Restricted Organ Expression Pattern of C2GnT3

A human RNA master blot (CLONTECH) was used for expression analysis. The cDNA-fragment of soluble C2GnT3 was used as a probe for hybridization. The probe was random primer-labeled using [$\alpha^{32}$P]dATP and and the Strip-EZ DNA labeling kit (Ambion). The membrane was probed for 6 h at 65° C. following the protocol of the manufacturer (CLONTECH) and washed five times for 20 min each at 65° C. with 2×SSC, 1% SDS and twice for 20 min each at 55° C. with 0.1×SSC, 0.5% SDS. A human multiple tissue Northern blot MTN II (CLONTECH), was probed as described (24), and washed twice for 10 min each at room temperature with 2×SSC, 0.1% SDS; twice for 10 min each at 55° C. with 1×SSC, 0.1% SDS; and once for 10 min with 0.1×SSC, 0.1% SDS at 55° C.

EXAMPLE 4

Analysis of C2GnT3 Gene Expression in Peripheral blood Mononuclear Cells

PCR analysis of C2GnT3 expression in resting and activated human blood cell fractions was performed using the primer pair:

```
TSHC118
(5'-GAGTCAGTGTGGAATTGAATAC-3', SEQ ID NO: 7)
and

TSHC126
(5'-CAACAGTCTCCTCAACCCTG-3', SEQ ID NO: 11).
```

PCR amplifications with primers specific for human C2GnT3 (C2GnT3) or GAPDH (G3PDH, supplied by the manufacturer) were performed on a normalized human blood cell cDNA panel (MTC from CLONTECH) for 31 cycles. Expression of C2GnT3 transcript was detected in all peripheral blood mononuclear cell (PBMC) fractions with particularly high levels of expression in CD4 and CD8 positive T-lymphocytes (FIG. 4).

EXAMPLE 5

Analysis of DNA Polymorphism of the C2Gn T3 Gene

Primer pairs such as:

```
TSHC123
(5'-GGGCAGCATTTGCCTAGTATG-3', SEQ ID NO: 10)
and

Figure 5:
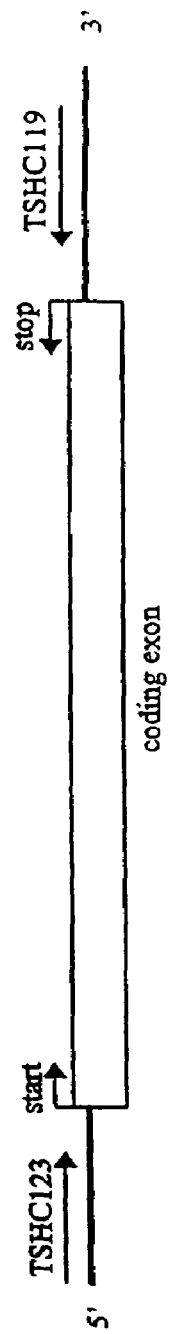
FIG. 5 is a schematic representation of forward and reverse PCR primers that can be used to amplify the coding exon of the C2GnT3 gene. The sequences of the primers TSHC119 and TSHC123 are also shown.

TSHC119
(5'-GATCTCTGATTTGGCTCAGTG-3', SEQ ID NO: 8)
``` as described in FIG. 5 have been used for PCR amplification of individual sequences of the coding exon. Each PCR product was subcloned and the sequence of 10 clones containing the appropriate insert was determined assuring that both alleles of each individual are characterized. Polymorphism of the amplified DNA can be analyzed using, e.g., DNA sequencing, single-strand conformational polymorphism (SSCP) or mismatch mutation.

From the foregoing it will be evident that, although specific embodiments of the invention have been described herein for purposes of illustration, various modifications may be made without deviating from the spirit and scope of the invention.

REFERENCES

1. Clausen, H. and Bennett, E. P. A family of UDP-GalNAc: polypeptide N-acetylgalactosaminyltransferases control the initiation of mucin-type O-linked glycosylation. Glycobiology 6: 635–646, 1996.
2. Piller, F., Piller, V., Fox, R. I., and Fukuda, M. Human T-lymphocyte activation is associated with changes in O-glycan biosynthesis. J. Biol. Chem. 263: 15146–15150, 1988.
3. Yang, J. M., Byrd, J. C., Siddiki, B. B., Chung, Y. S., Okuno, M., Sowa, M., Kim, Y. S., Matta, K. L., and Brockhausen, I. Alterations of O-glycan biosynthesis in human colon cancer tissues. Glycobiology 4: 873–884, 1994.

4. Yousefi, S., Higgins, E., Daoling, Z., Pollex-Kruger, A., Hindsgaul, O., and Dennis, J. W. Increased UDP-GlcNAc:Gal beta 1–3GalNAc-R (GlcNAc to GalNAc) beta-1,6-N-acetylglucosaminyltransferase activity in metastatic murine tumor cell lines. Control of polylactosamine synthesis. J. Biol. Chem. 266: 1772–1782, 1991.
5. Fukuda, M. Possible roles of tumor-associated carbohydrate antigens. Cancer Res. 56: 2237–2244, 1996.
6. Brockhausen, I., Yang, J. M., Burchell, J., Whitehouse, C., and Taylor-Papadimitriou, J. Mechanisms underlying aberrant glycosylation of MUC1 mucin in breast cancer cells. Eur. J. Biochem. 233: 607–617, 1995.
7. Brockhausen, I., Kuhns, W., Schachter, H., Matta, K. L., Sutherland, D. R., and Baker, M. A. Biosynthesis of O-glycans in leukocytes from normal donors and from patients with leukemia: increase in O-glycan core 2 UDP-GlcNAc:Gal beta 3 GalNAc alpha-R (GlcNAc to GalNAc) beta(1–6)-N-acetylglucosaminyltransferase in leukemic cells. Cancer Res. 51: 1257–1263, 1991.
8. Higgins, E. A., Siminovitch, K. A., Zhuang, D. L., Brockhausen, I., and Dennis, J. W. Aberrant O-linked oligosaccharide biosynthesis in lymphocytes and platelets from patients with the Wiskott-Aldrich syndrome. J. Biol. Chem. 266: 6280–6290, 1991.
9. Saitoh, O., Piller, F., Fox, R. I., and Fukuda, M. T-lymphocytic leukemia expresses complex, branched O-linked oligosaccharides on a major sialoglycoprotein, leukosialin. Blood 77: 1491–1499, 1991.
10. Springer, G. F. T and Tn, general carcinoma autoantigens. Science 224: 1198–1206, 1984.
11. Kumar, R., Camphausen, R. T., Sullivan, F. X., and Cumming, D. A. Core2 beta-1,6-N-acetylglucosaminyltransferase enzyme activity is critical for P-selectin glycoprotein ligand-1 binding to P-selectin. Blood 88: 3872–3879, 1996.
12. Williams, D. and Schachter, H. Mucin synthesis. I. Detection in canine submaxillary glands of an N-acetylglucosaminyltransferase which acts on mucin substrates. J. Biol. Chem. 255: 11247–11252, 1980.
13. Bierhuizen, M. F. and Fukuda, M. Expression cloning of a cDNA encoding UDP-GlcNAc:Gal beta 1–3-GalNAc-R (GlcNAc to GalNAc) beta 1–6GlcNAc transferase by gene transfer into CHO cells expressing polyoma large tumor antigen. Proc. Natl. Acad. Sci. U.S.A. 89: 9326–9330, 1992.
14. Schwientek, T., Yeh, J. C., Levery, S. B., Keck, B., Merkx, G., van Kessel, A. G., Fukuda, M., and Clausen, H. Control of O-glycan branch formation. Molecular cloning and characterization of a novel thymus-associated core 2 beta1,6-n-acetylglucosaminyltransferase. J. Biol. Chem. 275: 11106–11113, 2000.
15. Schwientek, T., Nomoto, M., Levery, S. B., Merkx, G., van Kessel, A. G., Bennett, E. P., Hollingsworth, M. A., and Clausen, H. Control of O-glycan branch formation. Molecular cloning of human cDNA encoding a novel beta1,6-N-acetylglucosaminyl-transferase forming core 2 and core 4. J. Biol. Chem. 274: 4504–4512, 1999.
16. Yeh, J. C., Ong, E., and Fukuda, M. Molecular cloning and expression of a novel beta-1,6-N-acetylglucosaminyltransferase that forms core 2, core 4, and I branches. J. Biol. Chem. 274: 3215–3221, 1999.
17. Baum, L. G., Pang, M., Perillo, N. L., Wu, T., Delegeane, A., Uittenbogaart, C. H., Fukuda, M., and Seilhamer, J. J. Human thymic epithelial cells express an endogenous lectin, galectin-1, which binds to core 2 O-glycans on thymocytes and T lymphoblastoid cells. J. Exp. Med. 181: 877–887, 1995.
18. Perillo, N. L., Marcus, M. E., and Baum, L. G. Galectins: versatile modulators of cell adhesion, cell proliferation, and cell death. J. Mol. Med. 76: 402–412, 1998.
19. Perillo, N. L., Pace, K. E., Seilhamer, J. J., and Baum, L. G. Apoptosis of T cells mediated by galectin-1. Nature 378: 736–739, 1995.
20. Devereux, J., Haeberli, P., and Smithies, O. A comprehensive set of sequence analysis programs for the VAX. Nucleic Acids Res. 12: 387–395, 1984
21. Altschul, S. F., Gish, W., Miller, W., Myers, E. W., and Lipman, D. J. Basic local alignment search tool. J. Mol. Biol. Oct. 5, 1990. 215: 403–410,
22. Bierhuizen, M. F., Maemura, K., Kudo, S., and Fukuda, M. Genomic organization of core 2 and I branching beta-1,6-N-acetylglucosaminyltransferases. Implication for evolution of the beta-1,6-N-acetylglucosaminyltransferase gene family. Glycobiology 5: 417–425, 1995.
23. Almeida, R., Amado, M., David, L., Levery, S. B., Holmes, E. H., Merkx, G., van Kessel, A. G., Rygaard, E., Hassan, H., Bennett, E., and Clausen, H. A family of human beta4-galactosyltransferases. Cloning and expression of two novel UDP-galactose: beta-N-acetylglucosamine beta1,4-galactosyltransferases, beta4Gal-T2 and beta4Gal-T3. J. Biol. Chem. 272: 31979–31991, 1997.
24. Bennett, E. P., Hassan, H., and Clausen, H. cDNA cloning and expression of a novel human UDP-N-acetyl-alpha-D-galactosamine. Polypeptide N-acetylgalactosaminyltransferase, GalNAc-T3. J. Biol. Chem. 271: 17006–17012, 1996.
25. Wandall, H. H., Hassan, H., Mirgorodskaya, E., Kristensen, A. K., Roepstorff, P., Bennett, E. P., Nielsen, P. A., Hollingsworth, M. A., Burchell, J., Taylor-Papadimitriou, J., and Clausen, H. Substrate specificities of three members of the human UDP-N-acetyl-alpha-D-galactosamine: Polypeptide N-acetylgalactosaminyltransferase family, GalNAc-T1, -T2, and -T3. J. Biol. Chem. 272: 23503–23514, 1997.
26. Matteucci, M. D. and Caruthers, M. H. J. Am. Chem. Soc. 103: 3185–3191. 1981.
27. Yoo, Y., Rote, K., and Rechsteiner, M. Synthesis of peptides as cloned ubiquitin extensions. J. Biol. Chem. 264: 17078–17083, 1989.

The invention claimed is:

1. An isolated UDP-N-Acetylglucosamine: Galactose β1,3 N-Acetylgalactosamine-α-R β1,6 N-Acetylglucosaminyl transferase (C2GnT3) polypeptide having glycosyltransferase activity and at least 80% amino acid sequence identity to the amino acid sequence of SEQ ID NO: 2.

2. The isolated C2GnT3 polypeptide of claim 1, wherein said amino acid sequence identity is at least 85%.

3. A UDP-N-Acetylglucosamine: Galactose β1,3 N-Acetylgalactosamine-α-R β1,6 N-Acetylglucosaminyl transferase (C2GnT3) polypeptide produced by a method comprising:
(i) introducing into a host cell an isolated DNA molecule encoding a human C2GnT3 polypeptide, or a DNA construct comprising a DNA sequence encoding a C2GnT3 polypeptide;
(ii) growing the host cell under conditions suitable for human C2GnT3 expression; and
(iii) isolating C2GnT3 polypeptide produced by the host cell,
wherein said C2GnT3 polypeptide has glycosyltransferase activity and is at least 80% identical to SEQ ID NO: 2.

4. The C2GnT3 polypeptide of claim 3, wherein said C2GnT3 polypeptide is at least 85% identical to SEQ ID NO: 2.

* * * * *

SEQUENCE LISTING

<160> NUMBER OF SEQ ID NOS: 17

<210> SEQ ID NO 1
<211> LENGTH: 1362
<212> TYPE: DNA
<213> ORGANISM: Human

<400> SEQUENCE: 1

| | | | | | |
|---|---|---|---|---|---|
| atgaagatat | tcaaatgtta | ttttaaacat | accctacagc | agaaagtttt | catcctgttt | 60 |
| ttaaccctat | ggctgctctc | tttgttaaag | cttctaaatg | tgagacgact | ctttccgcaa | 120 |
| aaagacattt | acttggttga | gtactccctca | agtacctcgc | cttttgtaag | aaacagatac | 180 |
| actcatgtta | aggatgaagt | caggtatgaa | gttaactgtt | cgggtatcta | tgaacaggag | 240 |
| cctttggaaa | ttggaaagag | tctggaaata | agaagaaggg | acatcattga | cttggaggat | 300 |
| gatgatgttg | tggcaatgac | cagtgattgt | gacatttatc | agactctaag | aggttatgct | 360 |
| caaaagcttg | tctcaaagga | ggagaaaagc | ttcccaatag | cctattcttt | ggttgtccac | 420 |
| aaagatgcaa | ttatggttga | aaggcttatc | catgctatat | acaaccagca | aatatttac | 480 |
| tgcatccatt | atgatcgtaa | ggcacctgat | accttcaaag | ttgccatgaa | caatttagct | 540 |
| aagtgcttct | ccaatatttt | cattgcttcc | aaattagagg | ctgtggaata | tgcccacatt | 600 |
| tccagactcc | aggctgattt | aaattgcttg | tcggaccttc | tgaagtcttc | aatccagtgg | 660 |
| aaatatgtta | tcaacttgtg | tgggcaagat | tttcccctga | agtcaaattt | tgaattggtg | 720 |
| tcagagttga | aaaaactcaa | tggagcaaat | atgttggaga | cggtgaaacc | cccaaacagt | 780 |
| aaattggaaa | gattcactta | ccatcatgaa | cttagacggg | tgccttatga | atatgtgaag | 840 |
| ctaccaataa | ggacaaacat | ctccaaggaa | gcacccccccc | ataacattca | gatatttgtt | 900 |
| ggcagtgctt | atttttgttttt | aagtcaagca | tttgttaaat | atattttcaa | caactccatc | 960 |
| gttcaagact | tttttgcctg | gtctaaagac | acatactctc | ctgatgagca | cttttgggct | 1020 |
| accttgattc | gggttccagg | aatacctggg | gagatttcca | gatcagccca | ggatgtgtct | 1080 |
| gatctgcaga | gtaagactcg | ccttgtcaag | tggaattact | atgaaggctt | tttctatccc | 1140 |
| agttgtactg | gatctcacct | tcgaagcgtg | tgtatttatg | gagctgcaga | attaaggtgg | 1200 |
| cttatcaaag | atggacattg | gttttgctaat | aaatttgatt | ctaaggtgga | ccctatcttg | 1260 |
| attaaatgct | tggcagaaaa | gcttgaagaa | cagcagagag | actggatcac | tttgccctca | 1320 |
| gaaaagttat | ttatggatag | aaatctcact | accacatcat | ga | | 1362 |

<210> SEQ ID NO 2
<211> LENGTH: 453
<212> TYPE: PRT
<213> ORGANISM: Human

<400> SEQUENCE: 2

Met Lys Ile Phe Lys Cys Tyr Phe Lys His Thr Leu Gln Gln Lys Val
1               5                   10                  15

Phe Ile Leu Phe Leu Thr Leu Trp Leu Leu Ser Leu Leu Lys Leu Leu
            20                  25                  30

Asn Val Arg Arg Leu Phe Pro Gln Lys Asp Ile Tyr Leu Val Glu Tyr
        35                  40                  45

Ser Leu Ser Thr Ser Pro Phe Val Arg Asn Arg Tyr Thr His Val Lys
    50                  55                  60

Asp Glu Val Arg Tyr Glu Val Asn Cys Ser Gly Ile Tyr Glu Gln Glu
65                  70                  75                  80

Pro Leu Glu Ile Gly Lys Ser Leu Glu Ile Arg Arg Arg Asp Ile Ile
                85                  90                  95

Asp Leu Glu Asp Asp Asp Val Val Ala Met Thr Ser Asp Cys Asp Ile
            100                 105                 110

Tyr Gln Thr Leu Arg Gly Tyr Ala Gln Lys Leu Val Ser Lys Glu Glu

```
                115                 120                 125
Lys Ser Phe Pro Ile Ala Tyr Ser Leu Val Val His Lys Asp Ala Ile
    130                 135                 140

Met Val Glu Arg Leu Ile His Ala Ile Tyr Asn Gln His Asn Ile Tyr
145                 150                 155                 160

Cys Ile His Tyr Asp Arg Lys Ala Pro Asp Thr Phe Lys Val Ala Met
                165                 170                 175

Asn Asn Leu Ala Lys Cys Phe Ser Asn Ile Phe Ile Ala Ser Lys Leu
            180                 185                 190

Glu Ala Val Glu Tyr Ala His Ile Ser Arg Leu Gln Ala Asp Leu Asn
        195                 200                 205

Cys Leu Ser Asp Leu Leu Lys Ser Ser Ile Gln Trp Lys Tyr Val Ile
210                 215                 220

Asn Leu Cys Gly Gln Asp Phe Pro Leu Lys Ser Asn Phe Glu Leu Val
225                 230                 235                 240

Ser Glu Leu Lys Lys Leu Asn Gly Ala Asn Met Leu Glu Thr Val Lys
                245                 250                 255

Pro Pro Asn Ser Lys Leu Glu Arg Phe Thr Tyr His His Glu Leu Arg
            260                 265                 270

Arg Val Pro Tyr Glu Tyr Val Lys Leu Pro Ile Arg Thr Asn Ile Ser
        275                 280                 285

Lys Glu Ala Pro Pro His Asn Ile Gln Ile Phe Val Gly Ser Ala Tyr
290                 295                 300

Phe Val Leu Ser Gln Ala Phe Val Lys Tyr Ile Phe Asn Asn Ser Ile
305                 310                 315                 320

Val Gln Asp Phe Phe Ala Trp Ser Lys Asp Thr Tyr Ser Pro Asp Glu
                325                 330                 335

His Phe Trp Ala Thr Leu Ile Arg Val Pro Gly Ile Pro Gly Glu Ile
            340                 345                 350

Ser Arg Ser Ala Gln Asp Val Ser Asp Leu Gln Ser Lys Thr Arg Leu
        355                 360                 365

Val Lys Trp Asn Tyr Tyr Glu Gly Phe Phe Tyr Pro Ser Cys Thr Gly
370                 375                 380

Ser His Leu Arg Ser Val Cys Ile Tyr Gly Ala Ala Glu Leu Arg Trp
385                 390                 395                 400

Leu Ile Lys Asp Gly His Trp Phe Ala Asn Lys Phe Asp Ser Lys Val
                405                 410                 415

Asp Pro Ile Leu Ile Lys Cys Leu Ala Glu Lys Leu Glu Glu Gln Gln
            420                 425                 430

Arg Asp Trp Ile Thr Leu Pro Ser Glu Lys Leu Phe Met Asp Arg Asn
        435                 440                 445

Leu Thr Thr Thr Ser
    450

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ggtttcaccg tctccaacat a                                              21

<210> SEQ ID NO 4
```

```
<211> LENGTH: 32
<212> TYPE: DNA
<213> ORGANISM: Artificial Sequence
<220> FEATURE:
<223> OTHER INFORMATION: Primer

<400> SEQUENCE: 4
cgaggatcca gaatgaagat attcaaatgt ta                              32

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
cgaggatccg caaaaagaca tttacttggt t                               31

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcgtaaggca cctgatactt                                            20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gagtcagtgt ggaattgaat ac                                         22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gatctctgat ttggctcagt g                                          21

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
agcgaattct tactatcatg atgtggtagt g                               31

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
```

```
gggcagcatt tgcctagtat g                                              21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
caacagtctc ctcaaccctg                                                20

<210> SEQ ID NO 12
<211> LENGTH: 1287
<212> TYPE: DNA
<213> ORGANISM: Human

<400> SEQUENCE: 12
atgctgagga cgttgctgcg aaggagactt ttttcttatc ccaccaaata ctactttatg    60
gttcttgttt tatccctaat caccttctcc gttttaagga ttcatcaaaa gcctgaattt    120
gtaagtgtca gacacttgga gcttgctggg gagaatccta gtagtgatat taattgcacc    180
aaagttttac agggtgatgt aaatgaaatc caaaaggtaa agcttgagat cctaacagtg    240
aaatttaaaa agcgccctcg gtggacacct gacgactata taaacatgac cagtgactgt    300 tcttcttttca tcaagagacg caaatatatt gtagaaccc ttagtaaaga agaggcggag    360
tttccaatag catattctat agtggttcat cacaagattg aaatgcttga caggctgctg    420
agggccatct atatgcctca gaatttctat tgcgttcatg tggacacaaa atccgaggat    480
tcctatttag ctgcagtgat gggcatcgct tcctgtttta gtaatgtctt tgtggccagc    540
cgattggaga gtgtggttta tgcatcgtgg agccgggttc aggctgacct caactgcatg    600
aaggatctct atgcaatgag tgcaaactgg aagtacttga taaatctttg tggtatggat    660
tttcccatta aaccaacct agaaattgtc aggaagctca agttgttaat gggagaaaac    720
aacctggaaa cggagaggat gccatcccat aaagaagaaa ggtggaagaa gcggtatgag    780
gtcgttaatg gaaagctgac aaacacaggg actgtcaaaa tgcttcctcc actcgaaaca    840
cctctctttt ctggcagtgc ctacttcgtg gtcagtaggg agtatgtggg gtatgtacta    900
cagaatgaaa aaatccaaaa gttgatggag tgggcacaag acacatacag ccctgatgag    960
tatctctggg ccaccatcca aaggattcct gaagtcccgg gctcactccc tgccagccat    1020
aagtatgatc tatctgacat gcaagcagtt gccaggtttg tcaagtggca gtactttgag    1080
ggtgatgttt ccaagggtgc tccctacccg ccctgcgatg gagtccatgt gcgctcagtg    1140
tgcattttcg gagctggtga cttgaactgg atgctgcgca acaccacttg tttgccaat    1200 aagtttgacg tggatgttga cctctttgcc atccagtgtt tggatgagca tttgagacac    1260
aaagctttgg agacattaaa acactga                                       1287

<210> SEQ ID NO 13
<211> LENGTH: 428
<212> TYPE: PRT
<213> ORGANISM: Human

<400> SEQUENCE: 13

Met Leu Arg Thr Leu Leu Arg Arg Arg Leu Phe Ser Tyr Pro Thr Lys
 1               5                  10                  15

Tyr Tyr Phe Met Val Leu Val Leu Ser Leu Ile Thr Phe Ser Val Leu
```

```
                    20                  25                  30
Arg Ile His Gln Lys Pro Glu Phe Val Ser Val Arg His Leu Glu Leu
            35                  40                  45
Ala Gly Glu Asn Pro Ser Ser Asp Ile Asn Cys Thr Lys Val Leu Gln
 50                  55                  60
Gly Asp Val Asn Glu Ile Gln Lys Val Lys Leu Glu Ile Leu Thr Val
 65                  70                  75                  80
Lys Phe Lys Lys Arg Pro Arg Trp Thr Pro Asp Asp Tyr Ile Asn Met
                85                  90                  95
Thr Ser Asp Cys Ser Ser Phe Ile Lys Arg Arg Lys Tyr Ile Val Glu
                100                 105                 110
Pro Leu Ser Lys Glu Glu Ala Glu Phe Pro Ile Ala Tyr Ser Ile Val
                115                 120                 125
Val His His Lys Ile Glu Met Leu Asp Arg Leu Leu Arg Ala Ile Tyr
                130                 135                 140
Met Pro Gln Asn Phe Tyr Cys Val His Val Asp Thr Lys Ser Glu Asp
145                 150                 155                 160
Ser Tyr Leu Ala Ala Val Met Gly Ile Ala Ser Cys Phe Ser Asn Val
                165                 170                 175
Phe Val Ala Ser Arg Leu Glu Ser Val Val Tyr Ala Ser Trp Ser Arg
                180                 185                 190
Val Gln Ala Asp Leu Asn Cys Met Lys Asp Leu Tyr Ala Met Ser Ala
                195                 200                 205
Asn Trp Lys Tyr Leu Ile Asn Leu Cys Gly Met Asp Phe Pro Ile Lys
                210                 215                 220
Thr Asn Leu Glu Ile Val Arg Lys Leu Lys Leu Leu Met Gly Glu Asn
225                 230                 235                 240
Asn Leu Glu Thr Glu Arg Met Pro Ser His Lys Glu Arg Trp Lys
                245                 250                 255
Lys Arg Tyr Glu Val Val Asn Gly Lys Leu Thr Asn Thr Gly Thr Val
                260                 265                 270
Lys Met Leu Pro Pro Leu Glu Thr Pro Leu Phe Ser Gly Ser Ala Tyr
                275                 280                 285
Phe Val Val Ser Arg Glu Tyr Val Gly Tyr Val Leu Gln Asn Glu Lys
                290                 295                 300
Ile Gln Lys Leu Met Glu Trp Ala Gln Asp Thr Tyr Ser Pro Asp Glu
305                 310                 315                 320
Tyr Leu Trp Ala Thr Ile Gln Arg Ile Pro Glu Val Pro Gly Ser Leu
                325                 330                 335
Pro Ala Ser His Lys Tyr Asp Leu Ser Asp Met Gln Ala Val Ala Arg
                340                 345                 350
Phe Val Lys Trp Gln Tyr Phe Glu Gly Asp Val Ser Lys Gly Ala Pro
                355                 360                 365
Tyr Pro Pro Cys Asp Gly Val His Val Arg Ser Val Cys Ile Phe Gly
                370                 375                 380
Ala Gly Asp Leu Asn Trp Met Leu Arg Lys His His Leu Phe Ala Asn
385                 390                 395                 400
Lys Phe Asp Val Asp Val Asp Leu Phe Ala Ile Gln Cys Leu Asp Glu
                405                 410                 415
His Leu Arg His Lys Ala Leu Glu Thr Leu Lys His
                420                 425

<210> SEQ ID NO 14
```

<211> LENGTH: 1317
<212> TYPE: DNA
<213> ORGANISM: Human

<400> SEQUENCE: 14

```
atggttcaat ggaagagact ctgccagctg cattacttgt gggctctggg ctgctatatg      60
ctgctggcca ctgtggctct gaaactttct ttcaggttga agtgtgactc tgaccacttg     120
ggtctggagt ccagggaatc tcaaagccag tactgtagga atatcttgta taatttcctg     180
aaacttccag caaagaggtc tatcaactgt tcagggtca cccgagggga ccaagaggca     240
gtgcttcagg ctattctgaa taacctggag gtcaagaaga agcgagagcc tttcacagac     300
acccactacc tctccctcac cagagactgt gagcacttca aggctgaaag gaagttcata     360
cagttcccac tgagcaaaga gaggtggag ttccctattg catactctat ggtgattcat     420
gagaagattg aaaactttga aaggctactg cgagctgtgt atgcccctca gaacatatac     480
tgtgtccatg tggatgagaa gtccccagaa actttcaaag gcggtcaa agcaattatt     540
tcttgcttcc caaatgtctt catagccagt aagctggttc gggtggttta tgcctcctgg     600
tccagggtgc aagctgacct caactgcatg aagacttgc tccagagctc agtgccgtgg     660
aaatacttcc tgaatacatg tgggacggac tttcctataa agagcaatgc agagatggtc     720
caggctctca agatgttgaa tgggaggaat agcatggagt cagaggtacc tcctaagcac     780
aaagaaaccc gctggaaata tcactttgag gtagtgagag acacattaca cctaaccaac     840
aagaagaagg atcctccccc ttataattta actatgttta cagggaatgc gtacattgtg     900
gcttcccgag atttcgtcca acatgttttg aagaaccta atcccaaca actgattgaa     960
tgggtaaaag acacttatag cccagatgaa caccttctggg ccaccttca gcgtgcacgg    1020
tggatgcctg gctctgttcc caaccacccc aagtacgaca tctcagacat gacttctatt    1080
gccaggctgg tcaagtggca gggtcatgag ggagacatcg ataagggtgc tccttatgct    1140
ccctgctctg gaatccacca gcgggctatc tgcgtttatg gggctgggga cttgaattgg    1200
atgcttcaaa accatcacct gttggccaac aagtttgacc caaaggtaga tgataatgct    1260
cttcagtgct tagaagaata cctacgttat aaggccatct atgggactga actttga      1317
```

<210> SEQ ID NO 15
<211> LENGTH: 438
<212> TYPE: PRT
<213> ORGANISM: Human

<400> SEQUENCE: 15

Met Val Gln Trp Lys Arg Leu Cys Gln Leu His Tyr Leu Trp Ala Leu
1               5                  10                  15

Gly Cys Tyr Met Leu Leu Ala Thr Val Ala Leu Lys Leu Ser Phe Arg
            20                  25                  30

Leu Lys Cys Asp Ser Asp His Leu Gly Leu Glu Ser Arg Glu Ser Gln
        35                  40                  45

Ser Gln Tyr Cys Arg Asn Ile Leu Tyr Asn Phe Leu Lys Leu Pro Ala
    50                  55                  60

Lys Arg Ser Ile Asn Cys Ser Gly Val Thr Arg Gly Asp Gln Glu Ala
65                  70                  75                  80

Val Leu Gln Ala Ile Leu Asn Asn Leu Glu Val Lys Lys Lys Arg Glu
                85                  90                  95

Pro Phe Thr Asp Thr His Tyr Leu Ser Leu Thr Arg Asp Cys Glu His
            100                 105                 110

```
Phe Lys Ala Glu Arg Lys Phe Ile Gln Phe Pro Leu Ser Lys Glu Glu
        115                 120                 125

Val Glu Phe Pro Ile Ala Tyr Ser Met Val Ile His Glu Lys Ile Glu
    130                 135                 140

Asn Phe Glu Arg Leu Leu Arg Ala Val Tyr Ala Pro Gln Asn Ile Tyr
145                 150                 155                 160

Cys Val His Val Asp Glu Lys Ser Pro Glu Thr Phe Lys Glu Ala Val
                165                 170                 175

Lys Ala Ile Ile Ser Cys Phe Pro Asn Val Phe Ile Ala Ser Lys Leu
            180                 185                 190

Val Arg Val Val Tyr Ala Ser Trp Ser Arg Val Gln Ala Asp Leu Asn
        195                 200                 205

Cys Met Glu Asp Leu Leu Gln Ser Ser Val Pro Trp Lys Tyr Phe Leu
    210                 215                 220

Asn Thr Cys Gly Thr Asp Phe Pro Ile Lys Ser Asn Ala Glu Met Val
225                 230                 235                 240

Gln Ala Leu Lys Met Leu Asn Gly Arg Asn Ser Met Glu Ser Glu Val
                245                 250                 255

Pro Pro Lys His Lys Glu Thr Arg Trp Lys Tyr His Phe Glu Val Val
            260                 265                 270

Arg Asp Thr Leu His Leu Thr Asn Lys Lys Asp Pro Pro Tyr
        275                 280                 285

Asn Leu Thr Met Phe Thr Gly Asn Ala Tyr Ile Val Ala Ser Arg Asp
    290                 295                 300

Phe Val Gln His Val Leu Lys Asn Pro Lys Ser Gln Gln Leu Ile Glu
305                 310                 315                 320

Trp Val Lys Asp Thr Tyr Ser Pro Asp Glu His Leu Trp Ala Thr Leu
                325                 330                 335

Gln Arg Ala Arg Trp Met Pro Gly Ser Val Pro Asn His Pro Lys Tyr
            340                 345                 350

Asp Ile Ser Asp Met Thr Ser Ile Ala Arg Leu Val Lys Trp Gln Gly
        355                 360                 365

His Glu Gly Asp Ile Asp Lys Gly Ala Pro Tyr Ala Pro Cys Ser Gly
    370                 375                 380

Ile His Gln Arg Ala Ile Cys Val Tyr Gly Ala Gly Asp Leu Asn Trp
385                 390                 395                 400

Met Leu Gln Asn His His Leu Leu Ala Asn Lys Phe Asp Pro Lys Val
                405                 410                 415

Asp Asp Asn Ala Leu Gln Cys Leu Glu Glu Tyr Leu Arg Tyr Lys Ala
            420                 425                 430

Ile Tyr Gly Thr Glu Leu
        435

<210> SEQ ID NO 16
<211> LENGTH: 1203
<212> TYPE: DNA
<213> ORGANISM: Human

<400> SEQUENCE: 16
atgcctttat caatgcgtta cctcttcata atttctgtct ctagtgtaat tatttttatc      60
gtcttctctg tgttcaattt tgggggagat ccaagcttcc aaaggctaaa tatctcagac     120
cctttgaggc tgactcaagt ttgcacatct tttatcaatg gaaaaacacg tttcctgtgg     180
aaaaacaaac taatgatcca tgagaagtct tcttgcaagg aatacttgac ccagagccac     240
```

```
tacatcacag cccctttatc taaggaagaa gctgactttc ccttggcata tataatggtc      300
atccatcatc actttgacac ctttgcaagg ctcttcaggg ctatttacat gccccaaaat      360
atctactgtg ttcatgtgga tgaaaaagca caactgaatt taaagatgc ggtagagcaa       420
ctattaagct gcttcccaaa cgcttttctg gcttccaaga tggaacccgt tgtctatgga      480
gggatctcca ggctccaggc tgacctgaac tgcatcagag atctttctgc cttcgaggtc      540
tcatggaagt acgttatcaa cacctgtggg caagacttcc ccctgaaaac caacaaggaa      600
atagttcagt atctgaaagg atttaaaggt aaaaatatca ccccagggt gctgccccca       660
gctcatgcaa ttggacggac taaatatgtc caccaagagc acctgggcaa agagctttcc      720
tatgtgataa gaacaacagc gttgaaaccg cctccccccc ataatctcac aatttacttt      780
ggctctgcct atgtggctct atcaagagag tttgccaact tgttctgca tgacccacgg       840
gctgttgatt tgctccagtg gtccaaggac actttcagtc ctgatgagca tttctgggtg      900
acactcaata ggattccagg tgttcctggc tctatgccaa atgcatcctg gactggaaac      960
ctcagagcta taaagtggag tgacatggaa gacagacacg gaggctgcca cggccactat     1020
gtacatggta tttgtatcta tggaaacgga gacttaaagt ggctggttaa ttcaccaagc     1080
ctgtttgcta acaagtttga gcttaatacc taccccctta ctgtggaatg cctagaactg     1140
aggcatcgcg aaagaaccct caatcagagt gaaactgcga tacaacccag ctggtatttt     1200
tga                                                                   1203

<210> SEQ ID NO 17
<211> LENGTH: 400
<212> TYPE: PRT
<213> ORGANISM: Human

<400> SEQUENCE: 17

Met Pro Leu Ser Met Arg Tyr Leu Phe Ile Ile Ser Val Ser Val
 1               5                  10                  15

Ile Ile Phe Ile Val Phe Ser Val Phe Asn Phe Gly Gly Asp Pro Ser
            20                  25                  30

Phe Gln Arg Leu Asn Ile Ser Asp Pro Leu Arg Leu Thr Gln Val Cys
        35                  40                  45

Thr Ser Phe Ile Asn Gly Lys Thr Arg Phe Leu Trp Lys Asn Lys Leu
    50                  55                  60

Met Ile His Glu Lys Ser Ser Cys Lys Glu Tyr Leu Thr Gln Ser His
65                  70                  75                  80

Tyr Ile Thr Ala Pro Leu Ser Lys Glu Glu Ala Asp Phe Pro Leu Ala
                85                  90                  95

Tyr Ile Met Val Ile His His Phe Asp Thr Phe Ala Arg Leu Phe
            100                 105                 110

Arg Ala Ile Tyr Met Pro Gln Asn Ile Tyr Cys Val His Val Asp Glu
        115                 120                 125

Lys Ala Thr Thr Glu Phe Lys Asp Ala Val Glu Gln Leu Leu Ser Cys
    130                 135                 140

Phe Pro Asn Ala Phe Leu Ala Ser Lys Met Glu Pro Val Val Tyr Gly
145                 150                 155                 160

Gly Ile Ser Arg Leu Gln Ala Asp Leu Asn Cys Ile Arg Asp Leu Ser
                165                 170                 175

Ala Phe Glu Val Ser Trp Lys Tyr Val Ile Asn Thr Cys Gly Gln Asp
            180                 185                 190

Phe Pro Leu Lys Thr Asn Lys Glu Ile Val Gln Tyr Leu Lys Gly Phe
```

-continued

```
               195                 200                 205
Lys Gly Lys Asn Ile Thr Pro Gly Val Leu Pro Pro Ala His Ala Ile
    210                 215                 220

Gly Arg Thr Lys Tyr Val His Gln Glu His Leu Gly Lys Glu Leu Ser
225                 230                 235                 240

Tyr Val Ile Arg Thr Thr Ala Leu Lys Pro Pro Pro His Asn Leu
                245                 250                 255

Thr Ile Tyr Phe Gly Ser Ala Tyr Val Ala Leu Ser Arg Glu Phe Ala
                260                 265                 270

Asn Phe Val Leu His Asp Pro Arg Ala Val Asp Leu Leu Gln Trp Ser
                275                 280                 285

Lys Asp Thr Phe Ser Pro Asp Glu His Phe Trp Val Thr Leu Asn Arg
    290                 295                 300

Ile Pro Gly Val Pro Gly Ser Met Pro Asn Ala Ser Trp Thr Gly Asn
305                 310                 315                 320

Leu Arg Ala Ile Lys Trp Ser Asp Met Glu Asp Arg His Gly Gly Cys
                325                 330                 335

His Gly His Tyr Val His Gly Ile Cys Ile Tyr Gly Asn Gly Asp Leu
                340                 345                 350

Lys Trp Leu Val Asn Ser Pro Ser Leu Phe Ala Asn Lys Phe Glu Leu
                355                 360                 365

Asn Thr Tyr Pro Leu Thr Val Glu Cys Leu Glu Leu Arg His Arg Glu
    370                 375                 380

Arg Thr Leu Asn Gln Ser Glu Thr Ala Ile Gln Pro Ser Trp Tyr Phe
385                 390                 395                 400
```